(12) United States Patent
Gallégo

(10) Patent No.: US 10,924,869 B2
(45) Date of Patent: Feb. 16, 2021

(54) USE OF PERIAURICULAR MUSCLE SIGNALS TO ESTIMATE A DIRECTION OF A USER'S AUDITORY ATTENTION LOCUS

(71) Applicant: Starkey Laboratories, Inc., Eden Prairie, MN (US)

(72) Inventor: Stéphane Gallégo, Vénissieux (FR)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

(21) Appl. No.: 16/271,281

(22) Filed: Feb. 8, 2019

(65) Prior Publication Data
US 2019/0253812 A1 Aug. 15, 2019

Related U.S. Application Data

(60) Provisional application No. 62/628,625, filed on Feb. 9, 2018.

(51) Int. Cl.
*H04R 25/00* (2006.01)
*H04S 7/00* (2006.01)
(Continued)

(52) U.S. Cl.
CPC ......... *H04R 25/407* (2013.01); *A61B 5/0488* (2013.01); *A61B 5/0492* (2013.01); *A61B 5/0496* (2013.01); *A61B 5/11* (2013.01); *A61B 5/12* (2013.01); *A61B 5/4851* (2013.01); *A61B 5/6817* (2013.01); *G06F 3/013* (2013.01);
(Continued)

(58) Field of Classification Search
CPC ... A61B 5/0488; A61B 5/0492; A61B 5/0496; A61B 5/11; A61B 5/12; A61B 5/4851; A61B 5/6817; G06F 3/013; G06F 3/015; H04R 1/406; H04R 1/1041; H04R 25/50; H04R 25/405; H04R 25/407;
(Continued)

(56) References Cited

U.S. PATENT DOCUMENTS 4,150,262 A 4/1979 Ono
5,161,533 A 11/1992 Prass et al.
(Continued)

FOREIGN PATENT DOCUMENTS

CN 105342613 A 2/2016
CN 205568942 U 9/2016
(Continued)

OTHER PUBLICATIONS

Examination Report from counterpart European Application No. 19707949.4, dated Feb. 26, 2020, 4 pp.
(Continued)

*Primary Examiner* — Brian Ensey
(74) *Attorney, Agent, or Firm* — Shumaker & Sieffert, P.A.

(57) ABSTRACT

A sound processing system measures one or more periauricular muscle signals from one or more periauricular muscles of a user. Additionally, the sound processing system computes, based on the periauricular muscle signals, an estimate of an angle corresponding to a direction of a current auditory attention locus of the user with respect to a reference point or plane. The sound processing system controls, based on the estimate of the angle, an operating characteristic of the sound processing system.

33 Claims, 11 Drawing Sheets

(51) Int. Cl.
| | |
|---|---|
| *A61B 5/0492* | (2006.01) |
| *A61B 5/00* | (2006.01) |
| *A61B 5/11* | (2006.01) |
| *A61B 5/0496* | (2006.01) |
| *H04R 1/10* | (2006.01) |
| *G06F 3/01* | (2006.01) |
| *A61B 5/12* | (2006.01) |
| *A61B 5/0488* | (2006.01) |
| *H04R 1/40* | (2006.01) |

(52) U.S. Cl.
CPC ........... *G06F 3/015* (2013.01); *H04R 1/1041* (2013.01); *H04R 25/505* (2013.01); *H04R 1/406* (2013.01); *H04R 25/405* (2013.01); *H04R 25/50* (2013.01); *H04R 2225/43* (2013.01); *H04R 2430/20* (2013.01); *H04S 7/302* (2013.01); *H04S 7/304* (2013.01)

(58) Field of Classification Search
CPC .............. H04R 25/505; H04R 2225/43; H04R 2430/20; H04S 7/302; H04S 7/304
See application file for complete search history.

(56) References Cited

U.S. PATENT DOCUMENTS

| | | | |
|---|---|---|---|
| 5,737,431 A | 4/1998 | Brandstein et al. | |
| 5,800,351 A | 9/1998 | Mann et al. | |
| 6,032,065 A | 2/2000 | Brown | |
| 6,422,999 B1 | 7/2002 | Hill | |
| 6,453,194 B1 | 9/2002 | Hill | |
| 6,625,481 B2 | 9/2003 | Bennett et al. | |
| 6,636,763 B1 | 10/2003 | Junker et al. | |
| 7,148,878 B2 | 12/2006 | Hong et al. | |
| 7,529,379 B2 | 5/2009 | Zurek et al. | |
| 7,554,549 B2 | 6/2009 | Sagar et al. | |
| 7,593,769 B1 | 9/2009 | Ettare | |
| 7,627,470 B2 | 12/2009 | Manabe et al. | |
| 7,914,468 B2 | 3/2011 | Shalon et al. | |
| 8,467,562 B2 | 6/2013 | Wada | |
| 8,504,146 B2 | 8/2013 | Joshi et al. | |
| 8,565,852 B2 | 10/2013 | Wada et al. | |
| 8,639,320 B2 | 1/2014 | Tomita et al. | |
| 8,768,477 B2 | 7/2014 | Spitzer et al. | |
| 8,894,718 B2 | 11/2014 | Sala et al. | |
| 8,989,857 B2 | 3/2015 | Heck | |
| 9,042,586 B2 | 5/2015 | Burns et al. | |
| 9,210,517 B2 | 12/2015 | Pontoppidan et al. | |
| 9,294,849 B2 | 3/2016 | Burns et al. | |
| 9,344,792 B2 | 5/2016 | Rundle | |
| 9,372,533 B1 | 6/2016 | Agrama | |
| 9,846,483 B2 | 12/2017 | Petrov | |
| 10,063,960 B2 | 8/2018 | Aase | |
| 10,121,063 B2 | 11/2018 | Von und zu Liechtenstein | |
| 10,137,363 B2 | 11/2018 | Parshionikar | |
| 10,191,558 B2 | 1/2019 | Parshionikar | |
| 2006/0058627 A1 | 3/2006 | Flaherty et al. | |
| 2006/0061544 A1 | 3/2006 | Min et al. | |
| 2008/0218472 A1 | 9/2008 | Breen et al. | |
| 2009/0005700 A1* | 1/2009 | Joshi ................ | A61B 5/0488 600/546 |
| 2009/0062680 A1 | 3/2009 | Sandford | |
| 2011/0125063 A1 | 5/2011 | Shalon et al. | |
| 2011/0276312 A1 | 11/2011 | Shalon et al. | |
| 2012/0116537 A1 | 5/2012 | Liebetanz | |
| 2012/0245655 A1 | 9/2012 | Spitzer et al. | |
| 2013/0123656 A1* | 5/2013 | Heck ................ | A63F 13/212 600/546 |
| 2014/0288447 A1 | 9/2014 | Luna et al. | |
| 2015/0063615 A1 | 3/2015 | Park et al. | |
| 2015/0157255 A1 | 6/2015 | Nduka | |
| 2016/0119726 A1* | 4/2016 | Pontoppidan ...... | G06K 9/00604 600/25 |
| 2016/0143079 A1 | 5/2016 | Keun et al. | |
| 2016/0243362 A1 | 8/2016 | Herhmann et al. | |
| 2016/0262689 A1 | 9/2016 | Batista | |
| 2017/0060256 A1 | 3/2017 | Heck et al. | |
| 2017/0180882 A1 | 6/2017 | Lunner et al. | |
| 2017/0318398 A1 | 11/2017 | Merks | |
| 2018/0074584 A1 | 3/2018 | Rüdiger et al. | |
| 2018/0107275 A1 | 4/2018 | Chen et al. | |
| 2018/0184916 A1 | 7/2018 | LeBoeuf et al. | |
| 2018/0193644 A1 | 7/2018 | Annoni et al. | |
| 2018/0263562 A1 | 9/2018 | LaPlante-Levesque et al. | |
| 2018/0321173 A1 | 11/2018 | Hanein et al. | |
| 2018/0368722 A1 | 12/2018 | Lunner et al. | |
| 2019/0008435 A1 | 1/2019 | Cakmak | |
| 2019/0025919 A1 | 1/2019 | Tadi et al. | |
| 2019/0052977 A1 | 2/2019 | Hannemann et al. | |
| 2019/0052978 A1 | 2/2019 | Hannemann et al. | |
| 2019/0265802 A1* | 8/2019 | Parshionikar ........... | G06F 3/012 |

FOREIGN PATENT DOCUMENTS

| | | |
|---|---|---|
| CN | 106175758 A | 12/2016 |
| CN | 106569607 A | 4/2017 |
| CN | 206470693 U | 9/2017 |
| CN | 108542387 A | 9/2018 |
| CN | 108670241 A | 10/2018 |
| CN | 109391891 A | 2/2019 |
| DE | 102015206450 A1 | 10/2016 |
| DE | 102017214164 B3 | 1/2019 |
| EP | 1519625 A2 | 3/2005 |
| EP | 1854404 B1 | 11/2007 |
| EP | 2442758 B1 | 5/2013 |
| EP | 2830493 A1 | 2/2015 |
| EP | 3105600 A | 12/2016 |
| EP | 3445067 A1 | 2/2019 |
| EP | 3445068 B1 | 1/2020 |
| GB | 2396421 A | 6/2004 |
| JP | 2019036959 A | 3/2019 |
| KR | 100516151 A | 2/2003 |
| KR | 101788709 A | 3/2016 |
| KR | 101785500 A | 8/2017 |
| KR | 20180056231 A | 5/2018 |
| KR | 101910021 B1 | 10/2018 |
| RU | 2312588 C1 | 12/2007 |
| WO | 2006033104 A1 | 3/2006 |
| WO | 2012129465 A1 | 9/2012 |
| WO | 2013144229 A1 | 10/2013 |
| WO | 2014055382 A1 | 4/2014 |
| WO | 2014152055 A2 | 9/2014 |
| WO | 2014176420 A1 | 10/2014 |
| WO | 2015017790 A | 2/2015 |
| WO | 2015123425 A1 | 8/2015 |
| WO | 2018027141 A1 | 2/2018 |
| WO | 2018103861 A1 | 6/2018 |
| WO | 2018218086 A1 | 11/2018 |

OTHER PUBLICATIONS

Wong et al., "Decoding Speech Sound Source Direction from Electroencephalography Data," ARO Abstracts vol. 39, ARO 39th Mid Winter Meeting, Feb. 21, 2016, p. 528.

International Search Report and Written Opinion of International Application No. PCT/US2019/017323, dated May 2, 2019, 15 pp.

Mirkovic et al., "Target Speaker Detection with Concealed EEG Around the Ear," Frontiers in Neuroscience, vol. 10, Article 349, Jul. 2016, 11 pp.

Rabinkin et al., "Optimum Microphone Placement for Array Sound Capture," The Journal of the Acoustical Society of America, Jul. 1997, 13 pp.

Valin et al., "Robust Sound Source Localization Using a Microphone Array on a Mobile Robot," Proceedings IEEE/RSJ International Conference on Intelligent Robots and Systems (IROS) 2003, Apr. 2004, pp. 1228-1233.

Moonen et al., "Horizontal Localization With Bilateral Hearing Aids: Without is Better Than With," The Journal of the Acoustical Society of America, vol. 119, No. 1, Jan. 2006, pp. 515-526.

(56) References Cited

OTHER PUBLICATIONS

O'Beirne et al., "The Post-Auricular Muscle Reflex (PAMR): Its Detection, Analysis, and Use as an Objective Hearing Test," retrieved from http://ir.canterbury.ac.nz/handle/10092/11083, Nov. 1998, 261 pp.
Stekelenburg et al., "Pericranial Muscular, Respiratory, and Heart Rate Components of the Orienting Response," Psychophysiology, vol. 39, Dec. 2002, pp. 707-722.
Keidser et al., "The Effect of Multi-Channel Wide Dynamic Range Compression, Noise Reduction, and the Directional Microphone on Horizontal Localization, Performance in Hearing Aid Wearers," International Journal of Audiology, vol. 45, No. 10, Feb. 7, 2006, pp. 563-579.
Kaneko, "Detecting the Direction of Listening with the EMG Signals Measured Behind Ears," Proceedings of the SIGCHI Conference on Human Factors in Computing Systems, Apr. 5-10, 2008, pp. 535-538.
Patuzzi et al., "Effects of Eye Rotation on the Sound-Evoked Post-Auricular Muscle Response (PAMR)," Hearing Research, vol. 138, Dec. 1999, pp. 133-146.
O'Beirne et al., "Basic Properties of the Sound-Evoked Post-Auricular Muscle Response (PAMR)," Hearing Research, vol. 138, Aug. 23, 1999, pp. 115-132.
Purdy et al., "The Post-Auricular Muscle Response: An Objective Electrophysiological Method for Evaluating Hearing Sensitivity," International Journal of Audiology, vol. 44, No. 11, Dec. 2005, pp. 625-630.
Cody et al., "Averaged Evoked Myogenic Responses in Normal Man," The Laryngoscope, vol. 79, No. 3, Apr. 1969, pp. 400-416.
Douek et al., "The Crossed Acoustic Response and Objective Tests of Hearing," Development Medicine and Child Neurology, vol. 16, No. 1, Feb. 1974, pp. 32-39.
Hackley et al., "Evidence for a Vestigial Pinna-Orienting System in Humans," Psychophysiology, vol. 52, No. 10, Jul. 2015, pp. 1263-1270.
Jacobson et al., "The Vestibular Evoked Myogenic Potential and Other Sonomotor Evoked Potentials," In: Auditory evoked potentials: basic principles and cl inical application, Chapter 27, 2007 (Applicant points out, in accordance with MPEP 609.04(a), that the year of publication, 2007, is sufficiently earlier than the effective U.S. filing date, so that the particular month of publication is not in issue.), pp. 572-593.
Kaneko et al., "Detecting the Direction of Listening with the Emg Signals Measured Behind Ears," In Proceedings of the SIGCHI Conference on Human Factors in Computing Systems, Apr. 5-10, 2008 , pp. 535-538.
Keidser et al., "The Effect of Multi-Channel Wide Dynamic Range Compression, Noise Reduction, and the Directional Microphone on Horizontal Localization Performance in Hearing Aid Wearers," International Journal of Audiology, vol. 45, No. 10, Nov. 2006, pp. 563-579.
Kiang et al., "Post-Auricular Electric Response to Acoustic Stimuli in Humans," Quarterly Progress Report, Lab of Electronics, M.I.T., No. 68, Jan. 15, 1963, pp. 218-226.
Patuzzi et al., "A Correlation Method for Detecting the Sound-Evoked Post-Auricular Muscle Response (PAMR)," Hearing Research, vol. 138, Dec. 1999, pp. 147-162.
Hackley et al., "Combined Use of Microflexes and Event-Related Brain Potentials as Measures of Auditory Selective Attention," Psychophysiology, vol. 24, No. 6, Nov. 1987, pp. 632-647.

Schmalfu et al., "Steer by Ear: Myoelectric Auricular Control of Powered Wheelchairs for Individuals with Spinal Cord Injury," Restorative Neurology and Neuroscience, vol. 34, No. 1, Jan. 2015, pp. 79-95.
Urban et al., "The Oculo-Auricular Phenomenon," Brain, vol. 116, Jun. 1993, pp. 727-738.
Yoshie et al., "Myogenic Evoked Potential Responses to Clicks in Man," Acta Oto-Laryngolica Supplementum, vol. 252, Feb. 1969, pp. 89-103.
De Grandis et al., "The Post-Auricular Response. A Single Motor Unit Study," Electroencephalography and Clinical Neurophysiology, vol. 50, May 21, 1980, pp. 437-440.
Douek et al., "The Crossed Acoustic Response," The Journal of Layngology and Otology, vol. 87, No. 8, Aug. 1973, pp. 711-726.
Douek et al., "A Single Average Crossed Acoustic Response," The Journal of Layngology and Otology, vol. 90, No. 11, Dec. 1976, pp. 1027-1032.
Dus et al., "The Click Evoked Post-Auricular Myogenic Response in Normal Subjects," Electroencephalography and Clinical Neurophysiology, vol. 39, Jun. 13, 1975, pp. 523-525.
Picton et al., "Human Auditory Evoked Potentials. I : Evaluation of Components," Electroencephalography and Clinical Neurophysiology, vol. 36, Aug. 1973, pp. 179-190.
Schmidt et al., "Co-Activation of the M. transversus auris with Eye Movements (Wilson's Oculo-Auricular Phenomenon) and with Activity in Other Cranial Nerves," Albrecht Von Graefe's Archive for Clinical and Experimental Ophthalmology, vol. 206, No. 4, Jul. 1978, pp. 227-236.
Streletz et al."Scalp Recorded Auditory Evoked Potentials and Sonomotor Responses: an Evaluation of Components and Recording Techniques," Electroencephalography and Clinical Neurophysiology, vol. 43, No. 2, Sep. 1977, pp. 192-206.
Colin, "Influence de la Surdite Neurosensorielle sur la Perception de la Hauteur Tonale," Neurosciences, University of Lyon, In the French Language with English Abstract, Dec. 12, 2016, 200 pp.
Guevara, "Amelioration de L'implant Cochleaire Oticon Neurelec et de son Pronostic : de L'ingenierie a la Stimulation Neurale," Neurosciences, University of Lyon, English Abstract Only, Dec. 18, 2015, 2 pp.
Ando et al., "CanalSense: Face-Related Movement Recognition System Based on Sensing Air Pressure in Ear Canals," Proceedings of the 30th Annual ACM Symposium on User Interface Software and Technology, Oct. 22-25, 2017, pp. 679-689.
Bedri et al., "Stick It In Your Ear: Building an In-Ear Jaw Movement Sensor," UbiComp/ISWC Adjunct, Sep. 7-11, 2015, pp. 1333-1338.
Carioli et al., "Piezoelectric Earcanal Bending Sensor," IEEE Sensors Journal, vol. 18, No. 5, Mar. 1, 2018, pp. 2060-2067.
Maag et al., "Barton: Low Power Tongue Movement Sensing with In-ear Barometers," 2017 IEEE 23rd International Conference on Parallel and Distributed Systems, Dec. 15-17, 2017, 9-16.
International Preliminary Report on Patentability from International Application PCT/US2019/017323, dated Aug. 20, 2020, 9 pp.
Thornton et al., "The Use of Post-Auricular Muscle Responses," The Journal of Laryngology & Otology, vol. 89, No. 10, Oct. 1975, pp. 997-1010.
Response to Examination Report dated Feb. 26, 2020, from counterpart European Application No. 19707949.4, filed Jun. 10, 2020, 19 pages.
Examination Report from counterpart European Application No. 19707979.4, dated Dec. 3, 2020, 4 pages.

\* cited by examiner

| | Shell | | Plug |
|---|---|---|---|
| | Receiver in the canal | | Electrical wires |
| | Shell | | |

| | Semi-custom (3 different, standard sizes) |
|---|---|
| | Receiver (standard RIC) |
| | Electrode (gold-plated 'nail' with round tip, 3mm diameter) |
| | Plug (to maintain receiver in place) |
| | Wires |

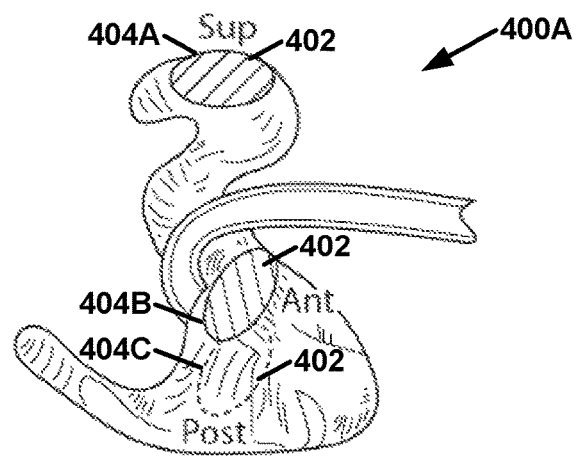
FIG. 4A
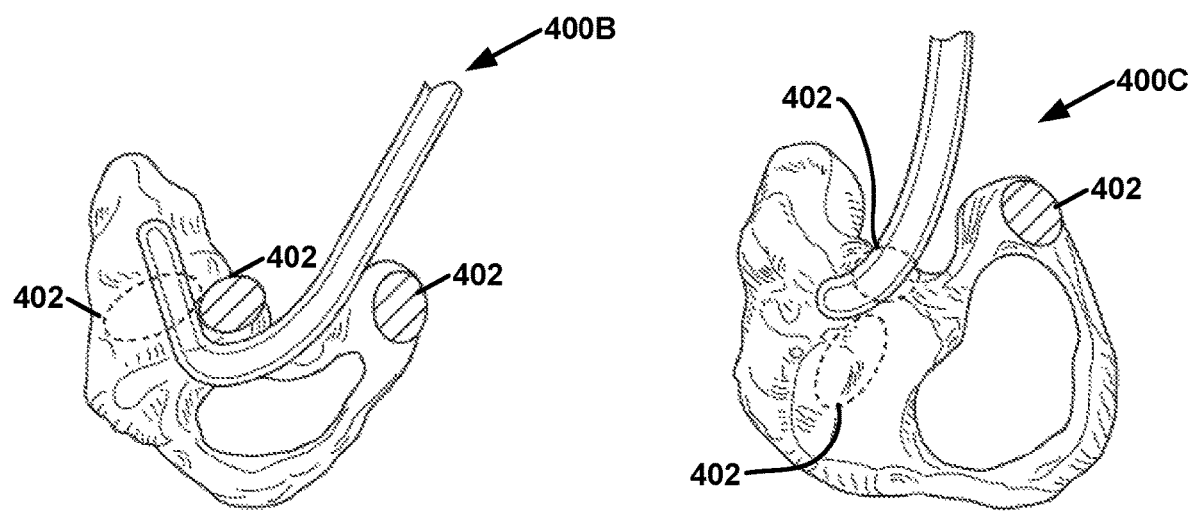
FIG. 4B
FIG. 4C

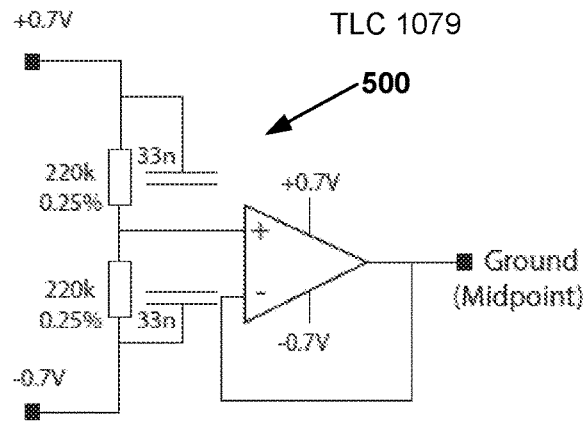
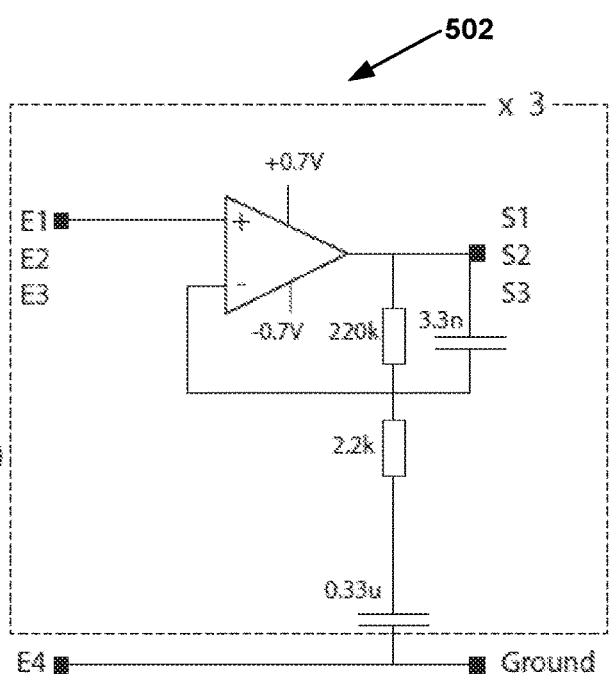
FIG. 5A                    FIG. 5B

Angle°
············ Anterior right
--------- Anterior left
———— Posterior left
– – – – Posterior left

USE OF PERIAURICULAR MUSCLE SIGNALS TO ESTIMATE A DIRECTION OF A USER'S AUDITORY ATTENTION LOCUS This application claims the benefit of U.S. Provisional Patent Application 62/628,625, filed Feb. 9, 2018, the entire content of which is incorporated by reference.

TECHNICAL FIELD

This disclosure relates to ear-wearable devices.

BACKGROUND

A sound processing system is a system of one or more devices designed to stimulate a user's auditory system. For example, a sound processing system may comprise one or more auditory prostheses, hearing aids, hearables, virtual-sound systems, headsets, earbuds, and other types of devices.

Typically, a sound processing system has at least one microphone and at least one speaker. The microphone detects sounds from the user's environment. The speaker (which may also be referred to as a "receiver") generates sounds directed into the user's ear canal. Because of signal distortions or information loss in a sound processing system, or of acoustic characteristics of a sound scene (e.g., low signal-to-noise ratio), or of limitations in auditory physiological or perceptual abilities (e.g., hearing impairment), the user may have difficulty with detecting, discriminating, identifying, locating, following over time, or other aspects of the perception of, a particular sound that to which the user wants to listen. For example, it may be difficult for the user to understand what a person that the user wants to listen to is saying, in the presence of other sound sources in the environment. A location of a sound that a user wants to hear, or listen to, is referred to as the user's auditory attention locus. Usually, but not necessarily, an auditory attention locus corresponds to the location of a sound source. A sound source can be real or virtual. For example, some sound reproduction or sound synthesis systems can recreate or simulate for the user, a sensation of sound sources at different positions.

To overcome listening difficulties in environments containing multiple sound sources, makers of sound processing systems have attempted to implement directional processing modes in ear-wearable devices. For example, almost all hearing-aids today have directional modes, in which sounds coming from some directions (e.g., behind the user) are attenuated relative to sounds coming from other directions (e.g., from in-front of the user). In this context, it is advantageous to have a system for automatically determining a user's auditory attention locus or, at least, the direction in which a user's auditory attention is directed. Previous attempts to design such a system have involved, for example, a smartphone application whereby the user can manually indicate their auditory attention locus. However, this type of solution involving manual input from the user is demanding (the user must provide manual input whenever their locus of attention changes), intrusive (the user must temporarily disengage from what they are doing to provide such input) and not discreet (the user must make gestures in order to interact manually with the input device, including gestures that may be visible to others). Other attempts to solve this problem have used electroencephalography (EEG) or electrooculography (EOG) to determine the user's auditory attention locus based on brain or eye signals.

SUMMARY

This disclosure describes techniques for inferring a user's auditory attention locus. Information concerning listening intentions of a user of a sound processing system (including, but not limited to, auditory prostheses, hearables, and virtual-sound systems), and in particular, information concerning the direction (angle) or location (angle and distance) of a listener's current auditory attentional focus, is difficult to obtain non-intrusively (i.e., without asking the user). The sound processing system may use such information in various applications, including but not limited to, applications involving a hearing device, such as a hearing-aid or hearable. For example, the sound processing system may use information regarding the direction or location of the user's current auditory attention locus to control a directional sound-processing algorithm on a hearing aid. Techniques of this disclosure may also be used in the context of a video game or a sensory-reeducation application (e.g., bio-feedback). As described herein, techniques of this disclosure may be used in situations in which it may be advantageous to infer non-intrusively (i.e., without the need for the user to alter their usual behavior) and/or covertly (i.e., non-observably to a third-party), using an ear-wearable device (e.g., hearing-aid, hearable, insertable earphones, etc.), the direction or locus where a user of the ear-wearable device is currently directing, or wanting to direct, his or her auditory attention.

In accordance with some techniques of this disclosure, a sound processing system (a) comprises at least one electrode placed in or close to, at least, one external ear (e.g., pinna or ear canal) of a user, for the purpose of measuring at least one electromyographic (EMG) signal generated by, at least, one of the user's periauricular muscles (PAMs), (b) uses the measurements to estimate an angle and/or a distance of the user's current focus of spatial auditory attention (i.e., auditory attention locus), and (c) uses the latter estimate(s) to control a directional or spatial sound-processing system. The directional or spatial sound-processing system may be implemented in hardware or software designed to process sound-related signals in a manner that depends on an angle of and/or a distance to a real or virtual sound source, relative to a spatial reference point.

In one example, this disclosure describes a method comprising: measuring one or more periauricular muscle signals from one or more periauricular muscles of a user; computing, based on the periauricular muscle signals, an estimate of an angle corresponding to a direction of a current auditory attention locus of the user with respect to a reference point or plane; and controlling, based on the estimate of the angle, an operating characteristic of a sound processing system.

In another example, this disclosure describes a sound processing system comprising: one or more electrodes configured to measure one or more periauricular muscle signals form one or more periauricular muscles of a user; and one or more processors configured to: compute, based on the periauricular muscle signals, an estimate of an angle corresponding to a direction of a current auditory attention locus of the user with respect to a reference point or plane; and control, based on the estimate of the angle, an operating characteristic of a sound processing system.

The details of one or more aspects of the disclosure are set forth in the accompanying drawings and the description below. Other features, objects, and advantages of the techniques described in this disclosure will be apparent from the description, drawings, and claims.

BRIEF DESCRIPTION OF DRAWINGS

FIG. 4A, FIG. 4B, and FIG. 4C show examples of custom earmolds which may be used in the context of custom intra-auricular ear-wearable devices according to techniques of this disclosure.

FIG. 5A shows an example circuit comprising a power supply and bridge voltage divider for a preamplifier, which may be used in conjunction with electrodes to measure PAM signals.

FIG. 5B shows an example electrode-signal preamplifier circuit which may be used in conjunction with electrodes to measure PAM signals.

DETAILED DESCRIPTION

In accordance with some techniques of this disclosure, a sound processing system (a) comprises at least one electrode placed in or close to, at least, one external ear (e.g., pinna or ear canal) of a user, for the purpose of measuring at least one electromyographic (EMG) signal generated by, at least, one of the user's periauricular muscles (PAMs), (b) uses the measurements to estimate an angle and/or a distance of the user's current focus of spatial auditory attention (i.e., auditory attention locus), and (c) uses the latter estimate(s) to control a directional or spatial sound-processing system. The directional or spatial sound-processing system may be implemented in hardware or software designed to process sound-related signals in a manner that depends on an angle of and/or a distance to a real or virtual sound source, relative to a spatial reference point.

Techniques of this disclosure may have one or more advantages over existing approaches for estimating a listener's auditory attention locus, such as approaches using electroencephalography (EEG) or electrooculography (EOG). For example, PAM signals are usually substantially larger than EEG and EOG signals when PAM signals are measured using electrodes placed in or close to the ear, which is a particularly convenient location, in the context of ear-wearable devices, such as hearing-aids or hearables. In another example, PAM activity is more directly related to the locus of auditory spatial attention. Therefore, the direction or locus of the user's auditory attention can be inferred more straightforwardly (e.g., potentially using fewer computational resources, less battery, and less delay) based on PAM signals than solely on EEG or EOG signals, which may be influenced by many more factors than auditory attention.

As noted above, this disclosure describes a sound processing system that measures PAM-related EMG signals and then uses such signals to control a directional or spatial sound processing system. In some examples, the sound processing system uses electrodes placed inside the ear canal and/or in the concha to detect the PAM-related EMG signals. In some examples, the sound processing system uses electrodes placed around the ear (e.g., on the skull) or on the pinna (e.g., as part of a circumaural or supra-aural headphone) to detect the PAM-related EMG signals.

In some examples, the sound processing system uses a difference between PAM-related EMG signals across the left and right sides and/or across different PAM muscles (e.g., anterior and posterior) on the same side of the head, to more reliably estimate a user's auditory attention locus. For instance, the sound processing system may compare differential PAM-related EMG signals (e.g., differential anterior-posterior PAM signals) on the right side of the head with differential PAM-related EMG signals on the left side of the head of a user, to estimate the angle and distance of a user's auditory-attention locus.

Figure 1:
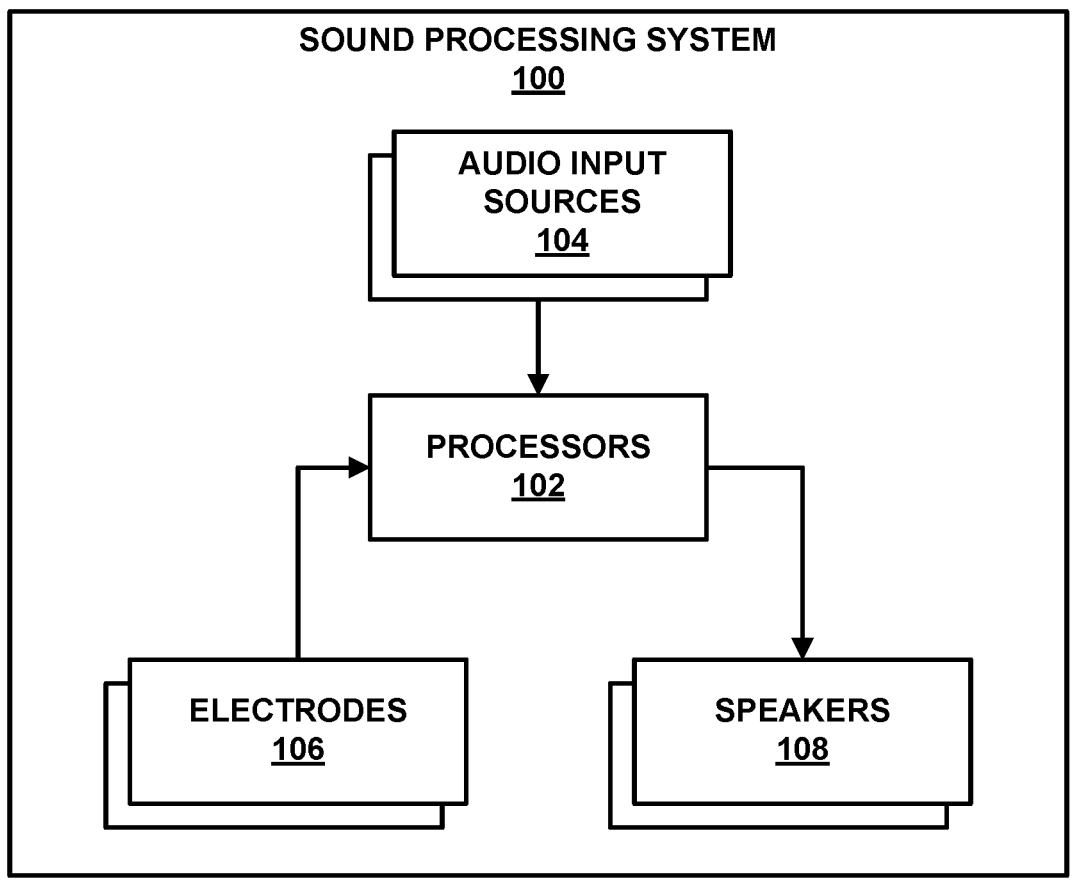
FIG. 1 is a conceptual diagram of an example sound processing system, in accordance with one or more techniques of this disclosure.

FIG. 1 illustrates an example sound processing system 100, in accordance with one or more aspects of this disclosure. In the example of FIG. 1, sound processing system 100 comprises one or more processors 102, one or more audio input sources 104, one or more electrodes 106, and one or more speakers 108. The components of sound processing system 100 (i.e., processors 102, audio input sources 104, electrodes 106, and speakers 108) may be incorporated into one or more physical devices. For example, each of the components of sound processing system 100 may be included in a single ear-wearable device. In another example, sound processing system 100 comprises two ear-wearable devices, each of which include one or more of processors 102, one or more of audio input sources 104, one or more of electrodes 106, and one or more of speakers 108. In another example, sound processing system 100 may comprise one or more ear-wearable devices, each of which may include one or more of processors 102, audio input sources 104, electrodes 106, and speakers 108, and sound processing system 100 may also comprise one or more separate devices, such as a smartphone or special purpose device, that comprises one or more of processors 102.

An ear-wearable device may comprise various types of devices designed to be worn in and/or on an ear of a wearer. For example, an ear-wearable device may comprise a hearing assistance device (e.g., a hearing aid device, a Personal Sound Amplification Product (PSAP), etc.), a wireless headset, a headphone, a wireless earbud, or another type of device. In another example, an ear-wearable device comprises a hearable with amplification and/or cancelation features.

In examples where sound processing system 100 comprises multiple devices, the devices of sound processing system 100 may communicate using wired or wireless communication technologies. For example, devices of sound processing system 100 may communicate wirelessly using a BLUETOOTH™ technology, a WIFI™ technology, or another type of wireless communication technology. In examples where processing system 100 comprises multiple processors 102, such processors may communicate with each other to accomplish the tasks described herein as being performed by processors 102.

Processor 102 may comprise one or more processing units, such as microprocessors, digital signal processors, application-specific integrated circuits, or other types of circuits. Audio input sources 104 provide audio data to processors 102. For example, audio input sources 104 may comprise one or more microphones. In some examples, audio input sources 104 may comprise software, such as video games or decoders of recorded media, for generating audio data. As described below, electrodes 106 include one or more electrodes that may be positioned to detect electromyographical (EMG) signals from one or more of a user's periauricular muscles (i.e., PAM signals). Speakers 108 output sound based on audio signals output by processors 102.

Sound processing system 100 may implement a variety of features that help a user of sound processing system 100 hear sounds. For example, processors 102 may generate audio signals that amplify the intensity of incoming sounds in audio signals generated by audio input sources 104, amplify the intensity of certain frequencies of the incoming sounds, translate or compress frequencies of the incoming sound, output recorded or dynamically-generated sound, or otherwise generate sound.

In accordance with techniques of this disclosure, processors 102 may implement a directional processing mode in which processors 102 selectively amplify sound originating from a particular direction (e.g., to the front of the wearer) and/or fully or partially cancel sound originating from other directions. In some examples, processors 102 may reduce noise by canceling out certain frequencies.

The directional processing mode may help wearers understand conversations occurring in crowds or other noisy environments. In other words, use of a directional processing mode may be useful in a situation in which a hearing-impaired user wears hearing-aids equipped with a directional-microphone system in an environment containing multiple sound sources, such as multiple talkers. In this situation, it may be advantageous for an algorithm controlling the directional-microphone system to have information regarding the direction and/or locus in space where the user is attending or wanting to attend. This disclosure may refer to the locus in space where the user is attending or wanting to attend as the user's current auditory attention locus.

Furthermore, in some examples, sound processing system 100 may help a wearer enjoy audio media, such as music or sound components of visual media, by outputting sound based on audio data wirelessly transmitted to sound processing system 100 (e.g., via audio input sources 104). In other words, the directional processing mode may be used when a user is listening to sounds (e.g., music, a television program, sounds from a video game) for which it is potentially advantageous to apply different signal-processing depending on the user's listening intentions, such as whether the user wishes to attend to sounds on the user's right or the left side. A specific instance of this type of situation involves a virtual ('3D') sound system, where different sounds in the simulated acoustic environment can be differentially enhanced, or attenuated, depending on their spatial positions and on the user's listening goals.

There are several challenges in implementing directional mode processing effectively. For example, estimating a user's current auditory attention locus is challenging for directional sound-processing algorithms such as those found on modern hearing-aids, e.g., 'beamformer' algorithms, which can selectively attenuate or amplify sounds coming from various directions, relative to sounds coming from other directions. Indeed, such systems are only beneficial to the user insofar as the sounds which they amplify are those which the user actually wants to listen to; failing this, directional sound-processing systems can actually be detrimental to the user. Additionally, it is challenging to locate the user's current auditory attention locus non-intrusively.

The techniques described in this disclosure may estimate the user's current auditory locus attention non-intrusively, using an ear-wearable device (e.g., a device placed inside the ear canal, in the concha, or around/behind the pinna), such as a hearing aid, where, or in which direction, the user of ear-wearable device 800 is currently focusing, or trying to focus, his/her auditory attention, and when that attentional focus is shifting.

The techniques of this disclosure for estimating the user's auditory attention locus may have use in a variety of scenarios including those discussed above. Additionally, the techniques of this disclosure for estimating the user's auditory attention locus may also be used in a sensory training or rehabilitation program involving an auditory attention component. For example, such a program might involve individuals with auditory, visual, or other sensory or neurological pathologies, who must be taught to better orient or focus their auditory attention in space.

Additionally, the techniques of this disclosure for estimating the user's auditory attention locus may help a user avoid front-back confusions. Front-back confusions are a frequent, and potentially life-threatening, perceptual error in hearing-aid wearers. (See e.g., Keidser et al., "The effect of multi-channel wide dynamic range compression, noise reduction, and the directional microphone on horizontal localization performance in hearing aid wearers," *International Journal of Audiology*, 45(10), pp. 563-579 (2006); Van den Bogaert, Klasen, Moonen, Van Deun, & Wouters, "Horizontal localization with bilateral hearing aids: without is better than with," *The Journal of the Acoustical Society of America*, 119(1), pp. 515-526 (2006). Specifically, the techniques of this disclosure for estimating the user's auditory attention locus may enable sound processing system 100 to determine whether the attention of a hearing-impaired user fitted bilaterally with hearing-aids is erroneously directed toward the user's back (e.g., due to the rear-facing orientation of microphones on the hearing-aids creating a misleading sound-location perception). This may be achieved by comparing the direction of the user's auditory attention (inferred using the disclosed techniques of this disclosure), to the estimated direction of a sound source of interest (e.g., speech) determined using a directional microphone system. If the listener's auditory attention is consistently directed toward the back, while speech is consistently coming from the front, this would indicate a consistent front-back confusion. This information could then be recorded and be accessible to the audiologist, the hearing-aid manufacturer, and/or the user. Alternatively, or in addition, the information could be used to trigger the activation of an algorithm on the hearing-aid (e.g., a directional-microphone mode or simulated pinna effect) designed to reduce or eliminate front-back confusions.

As described herein, sound processing system 100 may perform a three-step process. In a first step, electrodes 106 measure electromyographical signals from at least one of the periauricular muscles (PAMs) of a user. This disclosure may refer to an electromyographical signal from a PAM as a PAM signal. In a second step, processors 102 use the PAM signals to estimate a direction and/or distance of the user's current spatial auditory attention locus (i.e., where the listener's auditory attention is currently directed). In a third step, processors 102 use the resulting estimate to control a spatial or directional sound-processing system, for example, a beamformer. In other words, processors 102 may control, based on the estimate of an angle of a direction of the user's current auditory attention locus (and, in some instances, a distance to the user's current auditory additional locus), an operating characteristic of sound processing system 100. For instance, the operating characteristic may be a volume and/or frequency of sounds originating from the direction of the user's current auditory attention locus relative to sounds not originating from the direction and/or distance of the user's current auditory attention locus. The three steps are detailed below. However, this disclosure first explains why an ear-wearable device may use PAM signals for tracking a user's locus of spatial auditory attention.

The PAMs form part of a neuromusculuar pinna-orienting system, which in some animal species (e.g., canines and felines) is used to swivel the pinna(s) toward spatial locations corresponding to sound sources of interest. See e.g., Gobrecht, W. H., & Wilson, E., "*A system of human anatomy, general and special,*" Philadelphia: Blanchard and Lea (1858). In humans, the pinnas are strongly anchored to the skull, making it difficult for most individuals to appreciably move them. However, a few individuals can wiggle their pinnas, albeit feebly compared to felines. Nonetheless, the PAMs still contract depending on the position and volume of external sounds (reflex) as well as under volitional orientation of auditory attention, and these contractions, or micro-contractions, can be recorded using electrodes placed on the muscles. See e.g., O'Beirne, G. A., & Patuzzi, R. B., "Basic properties of the sound-evoked post-auricular muscle response (PAMR)," *Hearing Research*, 138(1-2), 115-132 (1999). In addition to being triggered reflexively in response to sound stimulation or eye rotations, PAM contractions can be elicited voluntarily by the individual; such volitional control of PAM contractions can be trained using bio-feedback methods. Therefore, PAM signals are prime candidates for non-intrusively tracking the focus of a listener's spatial auditory attention over time.

Figure 2:
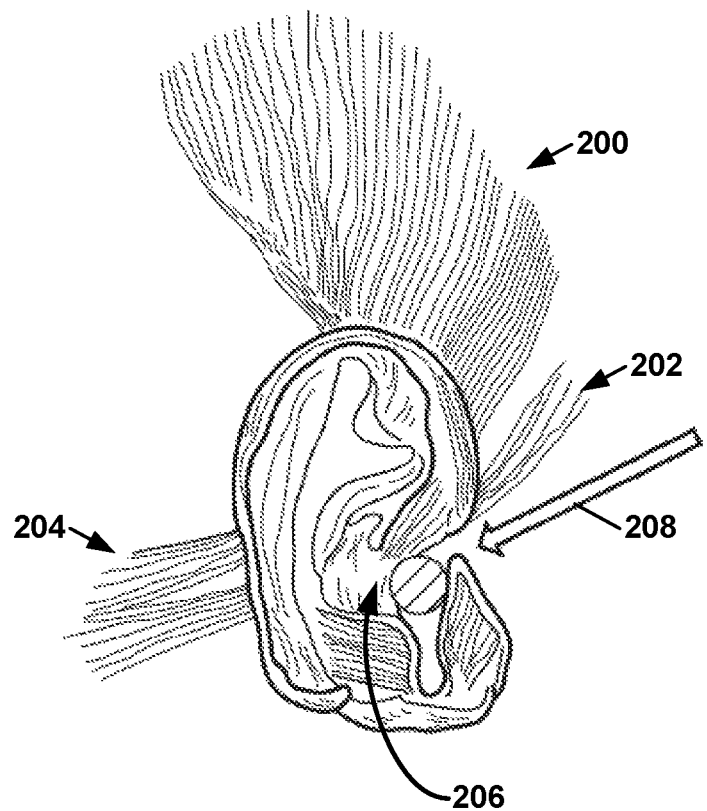
FIG. 2 is a conceptual diagram illustrating a human ear and periauricular muscles (PAMs), along with an example location for wear of the ear-wearable device, in accordance with a technique of this disclosure.

FIG. 2 is a conceptual diagram illustrating a human ear and PAMs, along with an example location for wear of an ear-wearable device, in accordance with a technique of this disclosure. As shown in FIG. 2, PAMs include an auricularis superior muscle 200, an auricularis anterior muscle 202, and an auricularis posterior muscle 204. The ear itself has a concha 206. Arrow 208 indicates a location in concha 206 where an ear-wearable device configured in accordance with techniques of this disclosure may be worn.

PAM activity is typically measured using electrodes 106 (FIG. 1). Some or all of electrodes 106 are located in, on, and/or around the user's ear. In contrast, some prior technologies have involved electrodes located behind the ear (i.e., on or near the mastoid bone), or above the ear (i.e., on the temporal bone). In accordance with the techniques of this disclosure, electrodes 106 in, on, and/or around the user's ear may be used with a behind-the-ear (BTE) device (e.g., a hearing aid or a hearable), in an in-the-ear (ITE) device, or in an in-the-canal (ITC) device. Sound processing system 100 may use electrodes 106 placed on, atop, or anterior to, and outside the ear canal or pinna for recording the activity of anterior PAM 202. Anterior to the ear canal means closer to the front of the body than the ear canal.

Figure 3A:
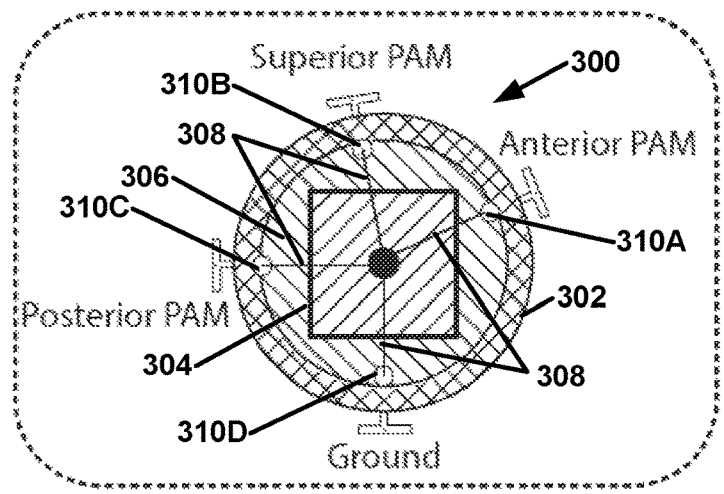
FIG. 3A is a conceptual diagram illustrating an ear-facing view of an example ear-wearable device designed for use inside an external ear canal of a user, in accordance with a technique of this disclosure.
Figure 3B:
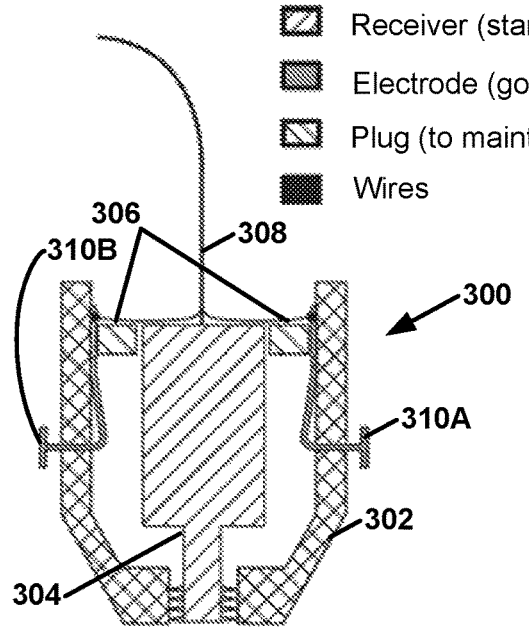
FIG. 3B is a schematic coronal plane view of the ear-wearable device, in accordance with a technique of this disclosure.

FIG. 3A is a conceptual diagram illustrating an ear-facing view of an example ear-wearable device 300 designed for use inside an external ear canal of a user, in accordance with a technique of this disclosure. Sound processing system 100 (FIG. 1) may include ear-wearable device 300. FIG. 3B is a schematic coronal plane view of ear-wearable device 300, in accordance with a technique of this disclosure. Ear-wearable device 300 measures PAM signals involving a receiver in the canal (MC), which can be placed entirely, or in part, inside a user's external ear canal (i.e., auditory meatus).

In the example of FIG. 3A and FIG. 3B, ear-wearable device 300 comprises a shell 302, a MC 304, a plug 306, electrical wires 308, and one or more electrodes. In the example of FIG. 3A, ear-wearable device 300 has four electrodes 310A, 310B, 310C, and 310D (collectively, "electrodes 310"). Electrodes 106 (FIG. 1) of sound processing system 100 may include electrodes 310. Three of electrodes 310 are for measuring PAM signals, and one of electrodes 310 serves as a reference. To optimize signal-to-noise ratio, the suggested locations for three of the four electrodes 310 are close to the expected insertion points of the muscle tendons around the ear canal; the fourth electrode is used for the ground (or reference) signal. Electrodes 310A, 310B, and 310C are positioned near the anatomical insertion points of the anterior, superior, and posterior PAMs in the ear canal. Electrode 310D is a ground electrode. The electrode locations shown in FIG. 3A and FIG. 3B are suggestive rather than prescriptive. Depending on the application, other or additional electrode locations may be used. The example illustrated in FIG. 3A and FIG. 3B is compatible with a BTE (with RIC) device, an in-the-ear (ITE) device, an in-the-canal (ITC) device, a completely-in-the-canal (CIC), or an invisible-in-the-canal form (IIC) hearing-aid or a hearable device.

Shell 302 may comprise a flexible body that is shaped to contain receiver 304 and hold electrodes 310 in the correct positions. Plug 306 may cover an open end of a cavity defined by shell 302. RIC 304 may provide sound delivery. Speakers 108 (FIG. 1) may include RIC 304. As shown in the example of FIG. 3C, electrodes 310 are supported by wires 308, which may act as springs pushing electrodes 310 against the skin of the ear canal to ensure good electrical contact between electrodes 310 and the skin.

FIG. 4A, FIG. 4B, and FIG. 4C show examples of custom earmolds 400A, 400B, and 400C (collectively, "earmolds 400") which may be used in the context of custom intra-auricular ear-wearable devices. FIGS. 4A-4C show example electrode locations 402 for measuring PAM signals from within the ear-canal and concha. In the example of FIGS.

4A-4C, filled ellipses correspond to example electrode locations directly visible with the current viewing angle; dashed ellipses correspond to example electrode locations on the opposite side, not directly visible with the current viewing angle.

In the example of FIG. 4A, electrode 404A measures signals from the superior auricular muscle. Electrode 404B measures signals from the anterior auricular muscle. Electrode 404C measures signals from the posterior auricular muscle. In the examples of FIGS. 4A-4C, at least one of electrodes 404 is located outside the ear canal, in the concha. Electrodes 106 (FIG. 1) may include electrodes 404A, 404B, and 404C. The designs illustrated in FIGS. 3A-3B and FIGS. 3A-3C are provided as examples. Other examples in accordance with techniques of this disclosure may use different designs, such as with fewer or more electrodes, and different electrode locations than those shown in FIGS. 3A-3B and FIGS. 4A-4C.

FIG. 5A shows an example circuit 500 comprising a power supply and bridge voltage divider for a preamplifier, which may be used in conjunction with electrodes 106 to measure PAM signals. FIG. 5B shows an example electrode-signal preamplifier circuit 502. Together, FIG. 5A and FIG. 5B represent a schema of electronic circuits, which may be used to collect and pre-amplify PAM signals. Processors 102 (FIG. 1) or other components of sound processing system 100 (FIG. 1) may include circuit 500 and circuit 502.

Electronic circuit 500 may measure EMG signals from the anterior, superior, and/or posterior PAMs. The operational-amplifier (op-amp) featured in circuit 500 may be one of the four op-amps featured in the TLC 1079 integrated circuit (IC). The TLC 1079 is a type of precision amplifier provide by Texas Instruments Inc. of Dallas, Tex. Advantageously, the TLC 1079 IC exists in ultra-CMS format, compatible with miniaturization constraints for an in-ear, or on-the-ear, device. Advantageously, the op-amps in the TLC 1079 IC use MOSFET technology, yielding a high input impedance compatible with the use of dry electrodes, which may be more convenient than wet electrodes in the context of consumer-device applications of the current disclosure. Additionally, this power supply/stabilizer design operates on 1.4V (−0.7V to +0.7V), compatible with battery voltage specifications used in current hearing aids (1.55V, 13-size battery), and its design features an arrangement of selected resistors and capacitors which, in combination with the op-amp, limit current leaks through the midpoint, thus limiting contamination of the EMG recordings by undesirable electronic noise.

In the example of FIG. 5B, the label '×3' is used to indicate that the plate (i.e., everything within the dashed line) can be replicated, up to 3 times, so as to obtain one preamplifier for each of the three periauricular muscles (posterior, anterior, superior), as needed for the application considered. The labels 'E1', 'E2', and 'E3' are used indicate that each replication of the plate should be connected to a different electrode. In most applications, these three electrodes are each connected to a different periauricular muscle. The label, 'E4', is used to denote a fourth electrode (e.g., electrode 310D of FIG. 3A), connected to the ground. The labels 'S1', 'S2', and 'S3' denote three amplified output signals, corresponding to the signals from the three electrodes labeled E1 through E3, respectively. In the example of FIG. 5A and FIG. 5B, resistors are shown by rectangles and capacitors are shown as parallel lines. The resistance values of the resistors are expressed in ohms and the capacitance values of the capacitors are expressed in farads.

As mentioned above, a second step comprises estimation of a direction or locus of the user's current auditory attentional focus. Particularly, processors 102 may estimate an angle of a direction between the user's current auditory attention locus and at least one reference point or plane. To estimate the angle between the user's current spatial auditory attention locus and at least one reference point or plane, processors 102 (FIG. 1) combine the PAM signals from at least one channel (where a channel is defined by a pair of electrodes including the ground electrode). In some examples, processors 102 estimate the angle based on a difference between the channels corresponding to the anterior and posterior PAMs on the same side of the user's head. Alternatively, or additionally, processors 102 may use the difference between one channel on the left and one channel on the right (for instance, the difference between the left and right posterior-PAM channels) to estimate the angle.

Figure 6A:
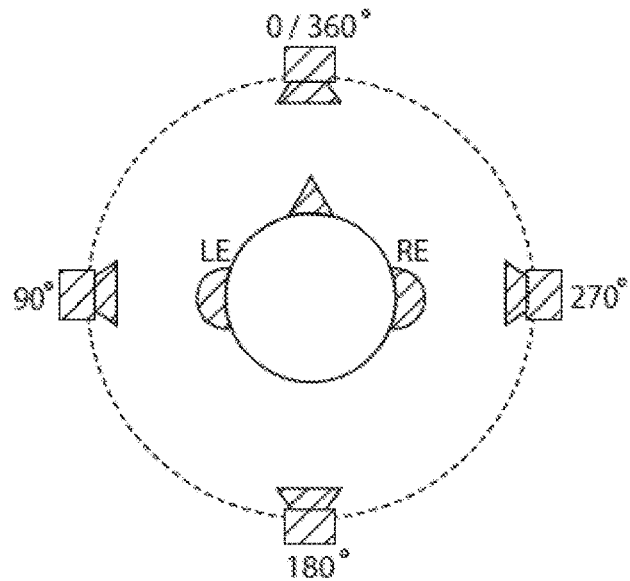
FIG. 6A is a schematic illustration of an example setup showing four different sound source locations around a user.
Figure 6B:
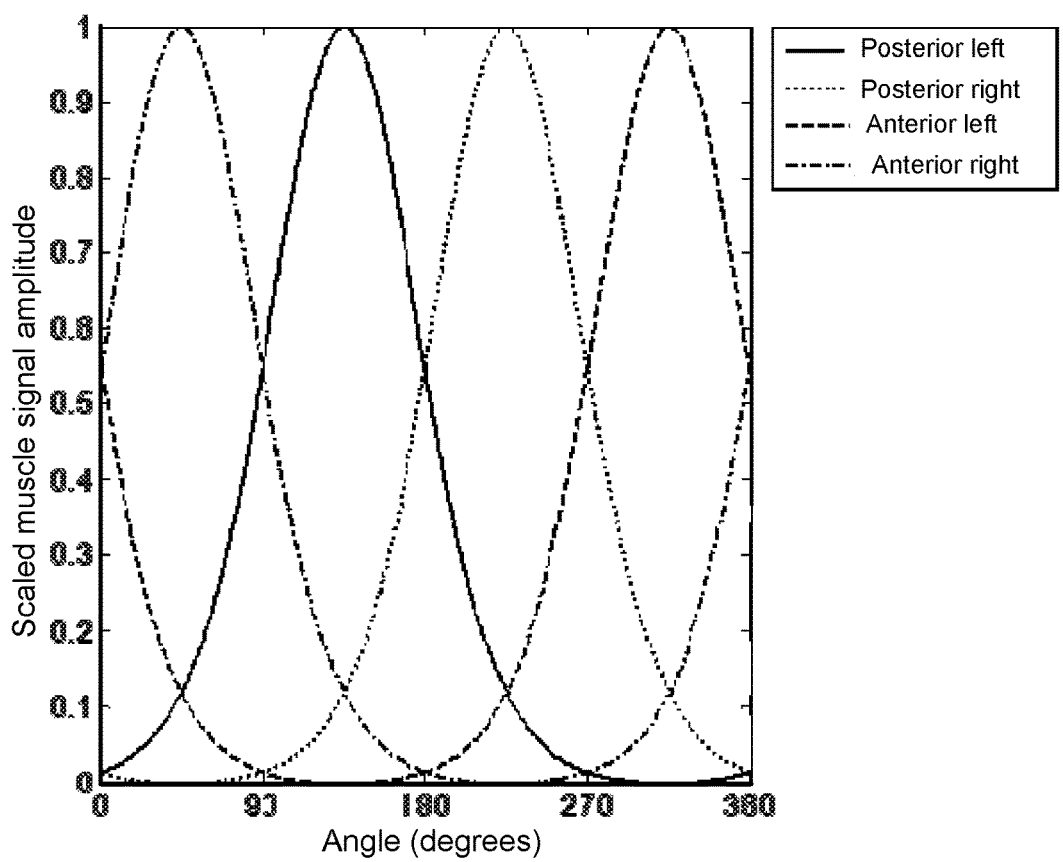
FIG. 6B illustrates an example of different signals corresponding to activities of anterior and posterior PAMs in the left and right side of the user's head.

FIG. 6A is a schematic illustration of an example setup showing four different sound source locations around a user. In the example of FIG. 6A, LE indicates left ear and RE indicates right ear. FIG. 6B illustrates an example of different signals corresponding to activities of anterior and posterior PAMs in the left and right side of the user's head. Together, FIG. 6A and FIG. 6B represent a schematic illustration of a principle for estimating the angle of a sound source in an azimuthal plane relative to a user's head, based on EMG signals from the posterior and anterior PAMs.

For instance, in the example of FIG. 6B, processors 102 may determine that the user's auditory attention locus is at an angle of 180° (i.e., directly behind the user) when the muscle activity for both the left and right posterior PAMs (expressed in FIG. 6B as scaled muscle signal amplitude) is at approximately 0.58 units, and the muscle activity for both the left and right anterior PAMs is 0.0 units. Similarly, processors 102 may determine that the user's auditory attention locus is at an angle of 90° (i.e., directly left of the user) when the muscle activity of the left posterior PAM and the muscle activity of the right anterior PAM are each at approximately 0.58 units.

In some examples, processors 102 determine the distance between a reference point and the user's auditory attention locus in addition to determining an angle between the direction of a user's auditory attention locus and a reference point or plane. The reference point may be one of the user's ears, a location midway between the user's ears, or another location. To determine the distance between the reference point and the user's auditory attention locus, processors 102 may combine signals from at least one channel on the left side of the user's head and at least one channel on the right side of the user's head. In one example, processors 102 compare the difference between the anterior and posterior channel signals on the right side to the difference between the anterior and posterior channel signals on the left side, according to a 'triangulation' formula.

In different examples, processors 102 may estimate the angle and/or distance between the user's current spatial auditory attention locus and at least one reference point or plane in different ways. These examples are described in this disclosure by way of illustration only.

In one example, processors 102 use PAM signals from one periauricular muscle, such as the posterior periauricular muscle corresponding to the user's right ear. Such PAM signals may be sufficient to obtain a first, coarse estimate of the angle of the direction of the user's current attentional locus since, for instance, the PAM signal varies as a function of this angle. In this situation, processors 102 may compute an estimate, á, of the angle, a, at time t, as:

$$á(t) = f(s(t),$$ (Eq. 1)

where s(t) is the PAM signal from the user's periauricular muscle at time t, and $f$ denotes a nonlinear function, which maps the PAM signal to an angle. Typically, but not necessarily, the function, $f$ is the inverse of a periodic function; for example, $$f(x)=\lambda^{-1}(x), \quad \text{(Eq. 2)}$$

where $\lambda^{-1}(\cdot)$ denotes the inverse of $\lambda(\cdot)$, and, $$\zeta(\theta)=\alpha \cdot (\exp(\kappa \cdot \cos(\pi\theta/180-\mu))^\gamma+\beta), \quad \text{(Eq. 3)}$$

where $\theta$ is an angle in degrees, while $\alpha$, $\beta$, $\gamma$, $\kappa$, and $\mu$ are parameters, the values of which may be estimated based on data obtained using a particular realization of the invention, for an individual user, or averaged across a group of users. In this context, $\mu$ is the angle for which the function reaches its maximum, $\kappa$ and $\gamma$ control the width and shape of the peak, and $\alpha$ and $\beta$ serve to shift and scale the function up or down. FIG. 6B shows an example of functions generated using Eq. 3, with $\gamma$ set to 1, and $\alpha$ and $\beta$ adjusted in such a way that the resulting function values span the interval (0;1). Note that the signal, s(t), need not reflect the activity of the periauricular muscle at time t only, and may reflect also contributions from the periauricular muscle at preceding time points. For instance, this would be the case in applications where s(t) is computed, through analog or digital circuitry, as a time-integral or time-weighted average of muscle activity signals unfolding over time.

In most applications, although not necessarily all applications, the function, $f$, is monotonic with s(t). Thus, the estimated angle increases or decreases with increasing or decreasing magnitude of activity of a periauricular muscle. In applications in which s(t) increases with the magnitude of activation of the posterior auricular muscle, $f$ is monotonically increasing with s(t) such that the estimated angle of the direction of the user's auditory attention locus with regard to a reference point situated in front of the user (defined as an angle of 0) increases with s(t).

In another example, to obtain an estimate of the angle of the direction of the user's attentional locus, processors 102 combine PAM signals across the left and right sides of the user's head. In this example, processors 102 compute the estimate, â(t), by subtracting at least one PAM signal on one side of the user's head from at least one PAM signal on the opposite side of the user's head. Denoting as $s_l(t)$ and $s_r(t)$ the PAM signals corresponding to the left side and the right side of the user's head, respectively, processors 102 may compute an estimate â, of the angle, a, at time t, as:

$$â(t)=g(f_l(s_l(t))-f_r(s_r(t))), \quad \text{(Eq. 4)}$$

where $f_l$ and $f_r$ are linear or nonlinear functions applied to the left and right signals prior to subtraction, and the operator g serves to map the result of the subtraction into an angle. Note that this allows for the case where no transformation is applied to the muscle signals prior to their subtraction, since the functions $f_l$ and $f_r$ may be each identified with a linear function having a slope of 1 and an intercept of 0. In some applications involving this estimation technique, the signals, $s_l(t)$ and $s_r(t)$, reflect the activity of the left and right posterior auricular muscles. In this situation, and if the functions, $f_l$ and $f_r$ are set to linear functions, then the mapping, g, may take the form of the inverse of a function, $g^{-1}$, defined as, $$g^{-1}(\theta)=\alpha \cdot (\exp(\kappa \cdot \cos(\pi\theta/180-\mu_l))^\gamma-\exp(\kappa \cdot \cos(\pi\theta/180-\mu_r))^\gamma), \quad \text{(Eq. 5)}$$

In a variant of the two examples above (illustrated using Equations 1 and 4), the signal, s(t), $s_l(t)$, or $s_r(t)$ corresponds to a linear or nonlinear combination of at least two PAM signals measured on the same side of the user's head. In some examples, although not necessarily all examples, processors 102 combine signals from the posterior and anterior auricular muscles in this way. Moreover, in some examples, although not necessarily all examples, the combination involves a subtraction. For example, denoting as $s_p(t)$ the signal corresponding to the posterior auricular muscle located on one side of the user's head, and $s_a(t)$ the signal corresponding to the posterior auricular muscle located on the same side of the user's head, processors 102 may compute the angle estimate, â(t) as:

$$â(t)=h(f_p(s_p(t))-f_a(s_a(t))), \quad \text{(Eq. 6)}$$

where $f_p$, $f_a$, and h are nonlinear functions used to map the muscle-activation signals and their combination into an angle estimate.

In another example, processors 102 mathematically or electronically combine signals from at least two periauricular muscles located on the right side of the user's head with signals from at least two periauricular muscles located on the left side of the user's head. In this example, processors 102 may compute the angle estimate as:

$$â(t)=v(h_l(f_{pr}(s_{pr}(t))-f_{ar}(s_{ar}(t)))-h_r(f_{pl}(s_{pl}(t))-f_{al}(s_{al}(t)))), \quad \text{(Eq. 7)}$$

where $s_{pr}$, $s_{ar}$, $s_{pl}$, and $s_{al}$ are signals corresponding to the posterior-right, anterior-right, posterior-left and anterior-left periauricular muscles, respectively, $f_{pr}$, $f_{ar}$, $f_{pl}$, and $f_{al}$ are linear or nonlinear functions applied to these signals (for example, these functions could be defined as illustrated in Eqs. 2 and 3), and $h_l$, $h_r$, and v, are nonlinear functions used to map intermediate variables into an angle estimate.

By combining signals from at least two periauricular muscles on one side of the user's head and signals from at least two periauricular muscles on the opposite side of the user's head, processors 102 may compute, in addition to an estimate of the angle between the direction of the user's attentional focus, an estimate of the distance between a reference point on the user (typically, the user's head) and the user's current auditory attention locus. The user's current auditory attention locus may correspond to an actual sound source in the user's physical environment, to a virtual sound source, or to an imaginary (or erroneously perceived) sound-source location. Processors 102 may obtain an estimate of the distance by combining said estimated angles (corresponding to the direction of the user's auditory attention) on the right side of the user's head, and the estimated angle on the left side of the user's head, using triangulation. Specifically, denoting as $â_r(t)$ and $â_l(t)$ estimates of the angles between (a) a line passing through the user's current auditory attention locus and a reference point on the user's right (for $â_r(t)$) or left (for $â_r(t)$) ear, and (b) a coronal plane passing through the user's left and right ear canals, and denoting as $d_{lr}$ the distance between the reference points on the user's left and right ears, processors 102 may compute the distance, denoted $d_r$, between the right-ear reference point and the current locus of the user's auditory attention focus as:

$$d_r=d_{lr} \sin(â_r(t)/180*\pi)/\sin((â_l(t)-â_r(t))/180*\pi). \quad \text{(Eq. 8)}$$

Similarly, processors 102 may compute the distance, denoted $d_l$, between the left-ear reference point and the current locus of the user's auditory attention focus as:

$$d_l=d_{lr} \sin(â_l(t)/180*\pi)/\sin((â_l(t)-â_r(t))/180*\pi). \quad \text{(Eq. 9)}$$

Angles in the above equations are in degrees.

Figure 7A:
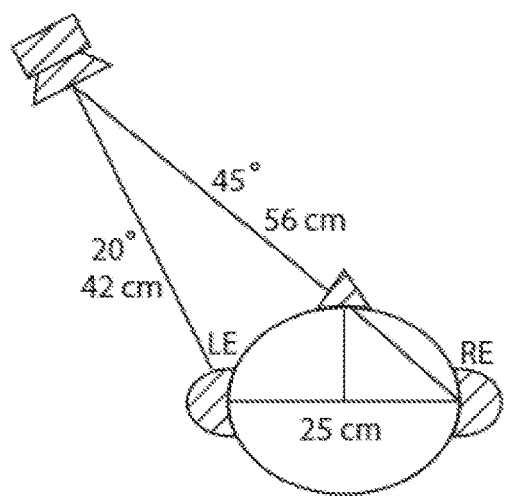
FIG. 7A is a schematic illustration of the 'triangulation' principle, which may be used to estimate the angle and distance of a sound source relative to a reference point.

FIG. 7A is a schematic illustration of the 'triangulation' principle, which may be used to estimate the angle and distance of a sound source relative to a reference point. For example, in the example of FIG. 7A, processors 102 (FIG. 1) determine $â_l(t)$ is approximately 70° and that $â_r(t)$ is approximately 45°. Moreover, in the example of FIG. 7A, $d_{lr}$ is assumed to be 25 cm. Accordingly, processors 102 may determine that the $d_l$ is equal to approximately 42 cm and that $d_r$ is equal to approximately 56 cm. In the example of FIG. 7A, the line between the user's ears may correspond to a reference plane; a point between the user's ears may correspond to a reference point.

Figure 7B:
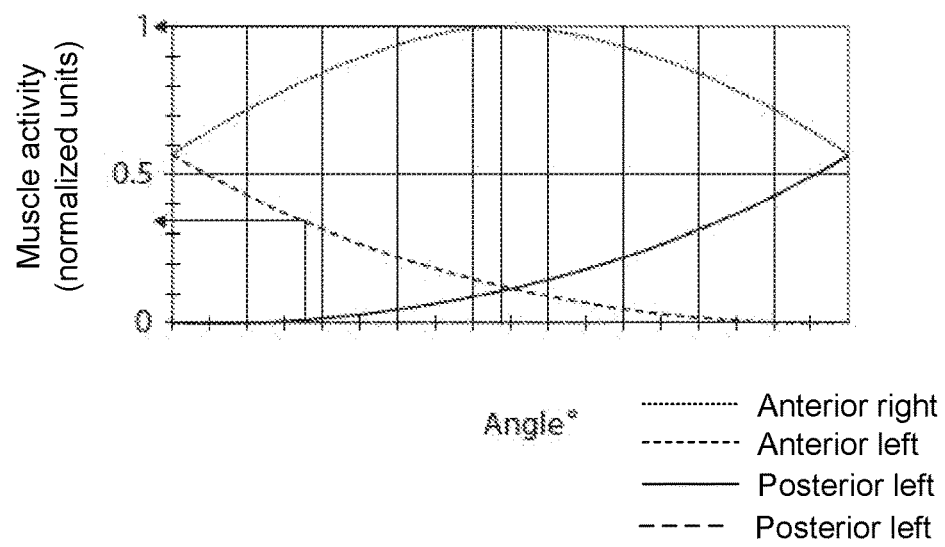
FIG. 7B is an example graph showing a technique for estimating an angle of a direction to a user's current auditory attention locus and the user's left ear and an angle of a direction to the user's current auditory attention locus and the user's right ear.

FIG. 7B is an example graph showing a technique for estimating an angle $â_l(t)$ of a direction to a user's current auditory attention locus and the user's left ear and an angle $â_r(t)$ of a direction to the user's current auditory attention locus and the user's right ear. As shown in the example of FIG. 7B, processors 102 (FIG. 1) may determine that $â_l(t)$ is equal to 20° relative to a vertical plane extending forward from the user's left ear (i.e., 70° relative to a horizontal line extending through the user's left and right ears) when the muscle activity of the left anterior auricular muscle is approximately 0.3 units (on a normalized measurement scale from 0 to 1, where 0 corresponds to no detectable muscle signal and 1 corresponds to the maximum muscle signal strength measurable by the device), and the muscle activity of the left posterior muscle is approximately 0.01 units (on the same normalized measurement scale). Similarly, processors 102 may determine that $â_r(t)$ is equal to 45° relative to a vertical plane extending forward from the user's right ear (i.e., 45° relative to the horizontal line extending through the user's left and right ears) when the muscle activity of the right anterior muscle is at 1.0 units and the muscle activity of the right posterior muscle is at 0.0 units.

Because the characteristics (e.g., absolute and relative amplitudes, latencies, signal-to-noise ratio, etc.) of the different PAM signals, and difference signals, can vary across individuals (e.g., depending on anatomical variability, skin conductance, and a myriad of other factors), as well as over time within a given user, processors 102 may use machine-learning algorithms that adapt, not only to a particular user, but also to changing conditions (i.e., changes in skin conductance depending on humidity, etc.) within a given user. Specifically, processors 102 may perform a 'tuning' procedure for the initial setting of the parameters of the algorithms that estimate the direction and distance based on PAM activity signals, as described above. In some examples, an initial setting is performed under well-controlled sound-stimulation conditions, with the device(s) placed on the user, and at least one sound source, positioned at (a) predefined distance(s) from a reference point placed, for instance, at a pre-defined position on the user's head. In some examples, processors 102 perform subsequent tunings each time the user puts ear-wearable device(s) (e.g., ear-wearable device 300 of FIG. 3A) in his/her ear(s). For these subsequent tunings, a single, readily-available sound source (e.g., smartphone) may be placed at an approximate position in front of the user, in a combination with a smartphone app to calibrate the algorithms. In some examples, the techniques described above may be advantageously supplemented with an apparatus that uses microphones to automatically estimate the angle and/or distance of a sound source in the user's environment (see, e.g., U.S. Pat. No. 5,737,431 A, filed Mar. 7, 1995, issued 1998; Daniel V. Rabinkin et al., "Optimum microphone placement for array sound capture," Proceedings of the SPIE, Vol. 3162, p. 227-239 (1997); and Valin, Michaud, Rouat, & Létourneau, "Robust Sound Source Localization Using a Microphone Array on a Mobile Robot," Proc. IEEE/RSJ International Conference on Intelligent Robots and Systems (IROS), pp. 1228-1233 (2003).

In addition, processors 102 may track drifts in the measured PAM signals, so that such drifts can be compensated for in the estimation of the direction and/or distance of the sound source. For example, suppose that a muscle-activity signal, s(t), follows a decreasing trend over the course of several minutes to a few hours; the ear-worn device, or an external device to which the ear-worn device sends information, can detect, compensate for, and extrapolate, such a drift by recording the muscle-activity signal at different moments, extracting relevant statistics (e.g., maximum value or upper decile) over successive time periods, and then comparing these values across the successive time periods. More advanced signal-processing or machine-learning algorithms (e.g., Kalman or particle filters) can also be used, to more accurately detect, track, extrapolate, and compensate for, any drift in muscle-activity signals over time.

A third step of the process uses the inferred direction of the user's current auditory attention locus to control an operating characteristic of a spatial or directional sound-processing system. A directional sound processing system is any processing device or algorithm that measures or computes the direction of arrival of a sound, or modifies a signal related to this sound in a direction-dependent manner. A spatial sound processing system is any device or algorithm that measures or computes spatial characteristics of a sound, such as its direction, distance, or spread (relative to one or several points or planes of reference), or that modifies a signal related to spatial characteristics of this sound. In this third step of processing, processors 102 may use the direction or position estimate derived in the previous step to control a directional or spatial sound-processing system.

In its simplest form, the target direction of a directional microphone system, such as a beamformer, is set to correspond to the currently-estimated direction of the user's auditory attention. More sophisticated versions of such processing involve a form of temporal smoothing, to avoid abrupt changes in the setting of the target direction for the directional sound system.

Other, more sophisticated processing performed during this third step could involve, but is not necessarily limited to, processors 102 using estimates of the location (i.e., direction and distance) of the user's auditory attentional locus. Processors 102 may use this advantageously in conjunction with a multi-microphone sound-processing system which can selectively attenuate, amplify, or otherwise process incoming sounds depending, not just on their angles of incidence, but also, depending on their distance, relative to the microphones.

It should be noted that this third step is optional, and could be replaced with other advantageous uses of the auditory-attention direction and or distance information estimated in the second step.

The techniques of this disclosure may contribute to the development of 'intelligent' hearing-aids or hearables which can infer, on a moment-by-moment basis, the user's listening intentions. In this context, it may be important to be able to determine the user's current auditory attention locus, or at least the direction of the user's current auditory attention locus. For instance, it may be important to determine whether the user currently attending (or trying to attend) to a sound source located in front of the user, to the user's right, to the user's left, or in the user's back. It may also be important to detect when the user's current auditory attention locus or the direction thereof changes, as happens when the user shifts the user's auditory attention from one talker to another in a multi-talker conversation.

Up to now, researchers in academia and in industry have focused on EEG or EOG signals. However, these have important shortcomings (poor signal-to-noise ratio, contamination by various artifacts, and/or need for computationally-heavy post processing), which currently limit their integration into products such as hearing-aids. In this context, PAM signals may be advantageous because firstly, they are usually markedly larger, and thus easier to measure reliably, from within or around the ear than EEG or EOG signals. Secondly, PAM signals may more straightforwardly relate to the user's current auditory attention locus or the direction thereof than EEG and EOG signals. This is because, in several mammals, the PAMs form part of a neuromuscular pinna-control system that evolved to improve sound detection and localization. Although in primates this system is largely vestigial, PAMs continue to be under the control of exogenous (reflex) and endogenous (deliberate) auditory attention. Given these advantages, the techniques of this disclosure may provide both a safer (i.e., more likely to succeed) and more direct route toward developing a user-brain-controlled hearing-aid/hearable than approaches based on EEG or EOG.

It is possible that one limitation of the techniques of this disclosure, over techniques using EEG signals for guiding the processing in hearing-aids or other ear-level devices, is that the information obtained from PAM signals is mostly limited to where in space a user's attention is directed, whereas EEG signals (if they can be reliably measured from within the ear in everyday life situations) may ultimately provide richer information about the user's listening goals. Hence, the techniques of this disclosure may be used in conjunction with EEG signals. For example, information derived from EMG signals from the periauricular muscles may be combined with information derived from EEG signals in order to improve the accuracy of an estimate of which sound source a listener is currently attending to in an auditory scene, or of where that sound source is located. To take an even more specific example of how this could work, there is a possibility of using brain activity measured using EEG measured using an ear-worn device, to infer which of two concurrent speech streams, corresponding to the voices of two talkers located in different positions in real or virtual soundspace, a listener is currently attending to (see, e.g., Mirkovic, Bleichner, De Vos, & Debener, "Target Speaker Detection with Concealed EEG Around the Ear," Frontiers in Neuroscience, vol. 10 (2016)). However, inferences obtained in this way are not always sufficiently accurate to support certain real-world applications of such technology (e.g., Mirkovic, Bleichner, De Vos, & Debener, 2016). The accuracy of the estimation of which voice a user wants to attend to can be improved by combining such EEG-based technology with the EMG-based aspect of the inventions described here, as the latter provides additional information concerning the direction or location to which the user is currently attending, or trying to attend.

One currently available approach for measuring a user's intentions is to have the user interact, manually or though voice commands, with the hearing device (e.g., using knobs on the hearing device), or with an external device connected to the hearing device (e.g., smartphone). For example, there exist smartphone apps with interfaces that let a user indicate the direction from which the sounds to which the user wishes to listen are coming; this information can then be used to inform the activation, or the setting of parameters, of algorithms on the hearing device, for instance, where to place the 'nulls' (maximum attenuation) of a directional-microphone system.

Another approach, which has been used previously in an attempt to gain information as to the direction in which a listener's auditory attention is directed, relies on head position or head movements. Directional sound systems on most hearing-aids today are based on this idea, and on the assumption that users tend to turn their head so as to face the sound source which they are wanting to listen to. Accordingly, most 'fixed' directional sound systems attenuate sounds coming from directions other than the front. Adaptive directional systems also exist, which attenuate sounds coming from directions other than one or several 'target' directions identified automatically by the device based on, for instance, the presence of salient speech-sound characteristics in this (or those) target direction(s).

Although not yet used in commercially-available hearing aids, another approach, which may be used in an attempt to obtain information regarding the listening intentions of a user of hearing device, relies on 'covert' measures, in particular, biophysical measures. These include electrophysiological measures of brain activity (using, e.g., EEG), or of movements of the eyes (using, e.g., EOG) or other body parts (e.g., finger, toe).

There are several disadvantages to the existing approaches. For example, the overt approach requires explicit, potentially frequent user motor input (manual or otherwise), which may be tedious for the user and may be unlikely to be used consistently over time by users of hearing-aids or hearables. Particularly, the difficulty comes from the fact that, in many real-life listening situations, the direction of auditory attention changes rapidly and often, as when, for instance, listening to a conversation with more than one interlocutor. Asking users to press a button to indicate every time that their auditory attentional focus changes may be unacceptable.

There are also disadvantages to approaches based solely on head movements. For example, one limitation of this approach is that sound sources of interest to the user are not always in front of the user. For instance, in a multi-talker conversation at a restaurant, head turns are not fast enough to ensure that the listener always faces the current talker. Information derived from PAM signals can usefully replace, or supplement, head-movement or head-position information.

There are also disadvantages to approaches based solely on eye movements (EOG). For example, eye movements are not straightforwardly related to auditory attention; they are also influenced by visual attention, and a myriad of other factors. Secondly, EOG signals are typically of smaller magnitude than PAM signals, especially when recorded using electrodes in or close to the ear.

Furthermore, there are disadvantages to approaches based solely on EEG. For example, EEG signals are of much smaller magnitude (i.e., have lower signal-to-noise ratios (SNR)) than PAM signals when recorded at or close to the ear. In another example, estimating the current direction or locus of a listener's auditory attention using EEG is much less straightforward computationally than estimating the same information based on PAM signals. The EEG-based approach also poses major basic research challenges (e.g., how to process the EEG?), computational challenges (e.g., can this processing be implemented on a miniature device?), and power-consumption (e.g., will it consume batteries?) challenges, which the PAM-based approach does not.

In contrast to overt measures, which require explicit and deliberate user interactions, the techniques of various examples of this disclosure use covert, implicit biophysical measures, which may be essentially seamless ('transparent') to the user and therefore, more likely to be accepted or tolerated by the user than overt (manual or other) deliberate interactions with the device. Furthermore, in contrast to previously-proposed covert measures for inferring the direction or locus of a listener's auditory attention, namely EEG and EOG, EMG signals from the PAMs are primarily, and almost exclusively, related to the direction or locus of the listener's auditory attention. Therefore, with the PAM signals, relatively little processing is performed in comparison to EEG or EOG signals to infer the direction or locus of the listener's auditory attention. In addition, because the PAMs are located very close to the ear, EMG signals generated by the activation of the PAMs are usually considerably larger, and thus easier to detect than EEG or EOG signals, when measured using electrodes placed in or near the ear.

Designers of video games, especially, those involving a form of virtual reality (VR), in particular, virtual audio (or '3D sound'), could find it advantageous to use techniques of this disclosure to verify that the spatial rendering of sound in a game is effective, or further, to estimate the accuracy of such rendering. To this aim, designers could play a sound to a user in a predetermined position of the virtual audio space under headphones, then use the techniques of this disclosure to infer the direction and/or locus of the listener's auditory attention, and confirm that the locus or direction thus inferred corresponds to the direction or locus of the virtual sound being played. If there is a consistent discrepancy, the test could be repeated using a sound at another location in virtual space, and adjustments could be made to parameters of the virtual-sound positioning algorithm so as to resolve the discrepancy between the attended spatial location and the actual sound location, thus allowing a more accurate positioning of sounds in virtual space than would otherwise be possible. Several other possible advantageous uses of the techniques of this disclosure in the context of the video-game industry are conceivable, but are not described here.

As briefly mentioned above, the techniques of this disclosure for determining a direction and/or locus of a user's auditory attention may be used in a reeducation, or 'training', context, where an individual with an auditory impairment, for instance, an auditory attention deficit, must be taught to improve his/her ability to focus or maintain his/her auditory attention. For example, a sound scene comprising two or more sound sources at virtual (simulated) locations could be played to the user under headphones or through insert earphones, and the user would be instructed to focus and maintain his attention on one of the sound sources. Using the techniques of this disclosure, the sound that the user is currently attending would be modified in some way (e.g., its volume could be slightly enhanced), as long as the user is attending to it (as determined using the techniques of this disclosure), thus providing a 'biofeedback' signal to the user; such biofeedback loop could form the basis of the training program. As an added benefit, using the techniques of this disclosure for estimating a direction and/or locus of the user's auditory attention, an operator or sound processing system 100 (automated mode) may verify that the user is indeed able to perform this spatially-selective-attention task.

In the context of this document, muscle signals are defined to mean any signal related to the voluntary or reflex stimulation of a muscle, whether or not this signal is accompanied or followed by an observable muscle contraction. The phrases 'directional sound processing system' or 'spatial sound processing system' mean any system that processes electrical signals related to sounds in a manner that depends on the location of the sound-generating sources, or the direction which these sounds form relative to a reference point, which may be on the device user.

Figure 8:
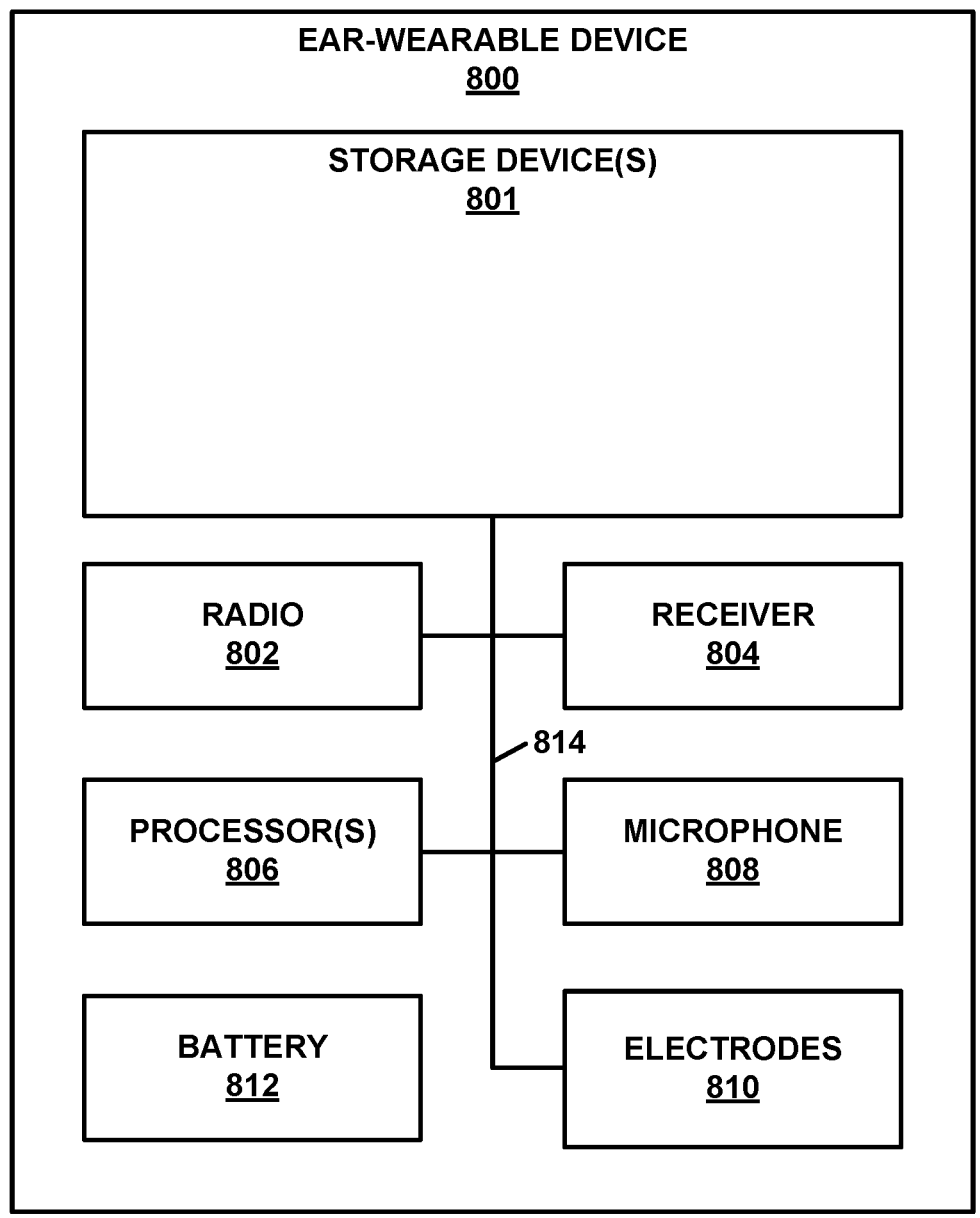
FIG. 8 is a block diagram illustrating example components of an ear-wearable device, in accordance with one or more aspects of this disclosure.

FIG. 8 is a block diagram illustrating example components of ear-wearable device 800, in accordance with one or more aspects of this disclosure. Sound processing system 100 (FIG. 1) may include ear-wearable device 800. In the example of FIG. 8, ear-wearable device 800 comprises one or more storage device(s) 801, a radio 802, a receiver 804, one or more processor(s) 806, a microphone 808, one or more electrodes 810, a battery 812, and one or more communication channels 814. Communication channels 814 provide communication between storage device(s) 801, radio 802, receiver 804, processor(s) 806, a microphone 808, and electrodes 810. Components 801, 802, 804, 806, 808, and 810 may draw electrical power from battery 812, e.g., via appropriate power transmission circuitry. Processors 102 (FIG. 1) may include processor(s) 806. Electrodes 106 (FIG. 1) may include electrodes 810. In other examples, ear-wearable device 800 may include more, fewer, or different components.

Storage device(s) 801 may store data. Storage device(s) 801 may comprise volatile memory and may therefore not retain stored contents if powered off. Examples of volatile memories may include random access memories (RAM), dynamic random access memories (DRAM), static random access memories (SRAM), and other forms of volatile memories known in the art. Storage device(s) 801 may further be configured for long-term storage of information as non-volatile memory space and retain information after power on/off cycles. Examples of non-volatile memory configurations may include flash memories, or forms of electrically programmable memories (EPROM) or electrically erasable and programmable (EEPROM) memories.

Radio 802 may enable ear-wearable device 800 to send data to and receive data from one or more other computing devices. For example, radio 802 may enable ear-wearable device 800 to send data to and receive data from other devices of sound processing system 100 (FIG. 1). Radio 802 may use various types of wireless technology to communicate. For instance, radio 802 may use Bluetooth, 3G, 4G, 4G LTE, ZigBee, WiFi, Near-Field Magnetic Induction (NFMI), or another communication technology.

Receiver 804 comprises one or more speakers for generating audible sound. Microphone 808 detects incoming sound and generates an electrical signal (e.g., an analog or digital electrical signal) representing the incoming sound. Processor(s) 806 may process the signal generated by microphone 808 to enhance, amplify, or cancel-out particular channels within the incoming sound. Processor(s) 806 may then cause receiver 804 to generate sound based on the processed signal. Furthermore, processor(s) 806 may implement the techniques of this disclosure for estimating a direction and/or locus of a user's auditory attention. In some examples, processor(s) 806 include one or more digital signal processors (DSPs).

In some examples, ear-wearable device 800 comprises a custom earmold or a standard receiver module at the end of a RIC cable. The additional volume in a custom earmold may allow room for components such as sensors (accelerometers, heartrate monitors, temp sensors), a woofer-tweeter, (providing richer sound for music aficionados), and an acoustic valve that provides occlusion when desired. In some examples, a six-conductor MC cable is used for in ear-wearable devices with sensors, woofer-tweeters, and/or acoustic valves.

Figure 9:
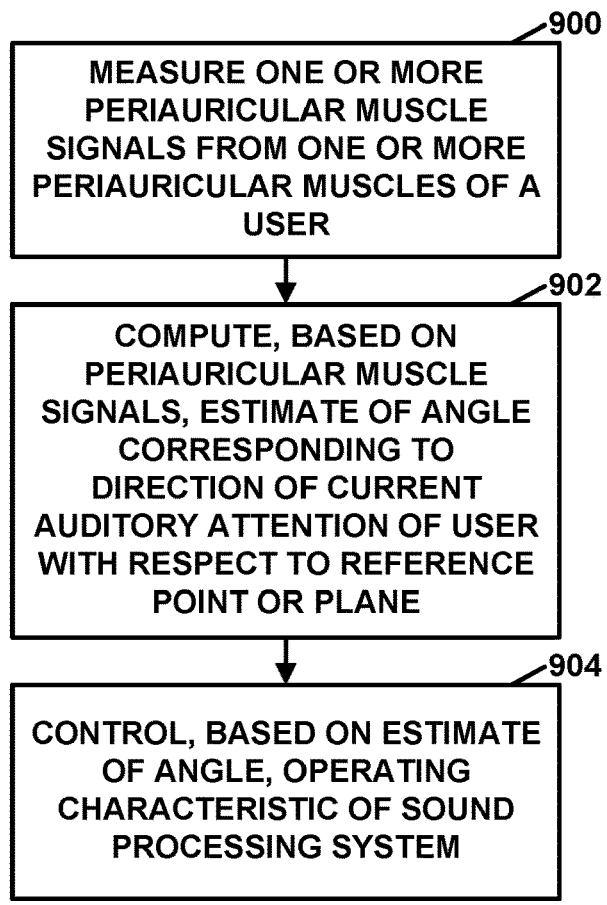
FIG. 9 is a flowchart illustrating an example operation of a sound processing system in accordance with a technique of this disclosure.

FIG. 9 is a flowchart illustrating an example operation of sound processing system 100 in accordance with a technique of this disclosure. The flowcharts of this disclosure are provided as examples. Other examples may include more, fewer, or different actions.

In the example of FIG. 9, electrodes 106 (FIG. 1) measure one or more periauricular muscle signals from one or more periauricular muscles of a user (900). Electrodes 106 may include one or more electrodes located at least partly inside an ear canal of the user. Furthermore, in some examples, electrodes 106 include one or more electrodes located at least partly inside a concha of the user. In some examples, electrodes 106 include one or more electrodes located at least partly atop or behind a pinna of the user. In some examples, electrodes 106 include one or more electrodes located at least partly anterior to an ear canal and pinna of the user and the one or more signals from the one or more periauricular muscles. In some examples, electrodes 106 measure a periauricular muscle signal from at least one anterior auricular muscle and at least one posterior auricular muscle on the same side of a head of the user.

In another example, electrodes 106 measure one or more signals from one or more periauricular muscles on a right side of the head of the user. In this example, electrodes 106 also measure one or more signals from one or more periauricular muscles on a left side of the head of the user. In some instances of this example, electrodes 106 measure signals from an anterior auricular muscle and a posterior auricular muscle on the right side of the head of the user and measure signals from an anterior auricular muscle and a posterior auricular muscle on the left side of the head of the user.

Furthermore, processors 102 may compute, based on the periauricular muscle signals, an estimate of an angle corresponding to a direction of a current auditory attention locus of the user with respect to a reference point or plane (902). In some examples where electrodes 106 measure one or more signals from one or more periauricular muscles on a right side of the head of the user and measure one or more signals from one or more periauricular muscles on a left side of the head of the user, processors 102 compute, based on the one or more signals from the one or more periauricular muscles on the right side of the head of the user and the one or more signals from the one or more periauricular muscles on the right side of the head of the user, an estimate of the distance corresponding to the current auditory attention locus of the user. For instance, processors 102 may use the triangulation techniques described elsewhere in this disclosure to determine the distance.

In some examples, processors 102 use the one or more periauricular muscle signals to compute an estimate of an elevation angle corresponding to the current auditory attention locus of the user, relative to a reference point or plane. The elevation angle may be a component (e.g., a z component) of the angle used in controlling an operating characteristic of sound processing system 100. For instance, in this example, as part of measuring the set of one or more periauricular muscle signals, one or more electrodes may measure a signal from a superior auricular muscle of the user. In this example, processors 102 may use a signal from the superior auricular muscle to compute the estimate of the elevation angle corresponding to the current auditory attention locus of the user, relative to the reference point or plane. For example, the processor could take as input a measure of the amplitude, or intensity, of the superior auricular muscle activity signal, and compute a monotonically increasing transformation of this input, such that higher muscle-activity signal amplitudes, or higher intensities, correspond to a higher estimated elevation angle relative to a transverse plane through the user's ear canals or other reference plane through the user's body. The transformation used for this purpose could be implemented using a look-up table, wherein each superior auricular muscle signal amplitude comprised within the range of amplitudes that can be measured by the device has a corresponding elevation-angle estimate. The values in such a table could be determined based on measurements of posterior auricular muscle activity signals for different elevations of a real, virtual, or imagined sound source. Such measurements could be performed, specifically, on the user of the system to obtain individual data, or on a group of individuals to obtain average data. Alternatively, the transformation of said muscle-activity signal amplitude into an estimate of the elevation angle could be implemented as a linear or nonlinear function. The parameters of such a function could be determined by computing the best fit (according to a maximum-likelihood, minimum squared error, or some other criterion) of said function to measurements of at least one posterior muscle-activity signal amplitude.

In some examples, sound processing system 100 comprises one or more electrodes for measuring eye signals. The eye signals comprise at least one of eye-movement signals of the user or eye-position signals of the user. For instance, the eye signals may comprise EOG signals. The electrodes for generating the EOG signals may be in the ear canal of the user, or they may be placed elsewhere, for example, closer to at least one of the two eyes of the user. Processors 102 may combine such eye signals with the periauricular muscle signals mathematically, in order to compute a combined signal. The combined signal may provide a better estimate of the angle corresponding to the direction of the user's current auditory attention locus, relative to the reference point or plane. For example, if the user's eyes move in the direction corresponding to the user's auditory attention target, the processor can compute a weighted mean of the target-angle estimate (in complex-number form) computed based on the eye-movement signal, and of the target-angle estimate (in complex-number form) computed based on the peri-auricular muscle signals, as follows, $$\hat{\theta}=\arg(w_a e(i\theta_a)+(1-w_a)e(i\theta_e)) \quad (\text{Eq. 10})$$

where $\theta_a$ is the angle of the user's auditory-attention target computed using periauricular-muscle signals only, $\theta_e$ is the angle of the user's auditory-attention target computed using eye signals only, $w_a$ is the relative weight of the angle information derived from peri-auricular muscle signals, and $\hat{\theta}$ is the resulting estimate of the user's auditory attention target, obtained by combining mathematically the periauricular-muscle and eye signals. If the relative weight, $w_a$, is chosen appropriately, a more accurate and precise estimate of the direction of the user's auditory attention can be obtained in this way, than might be possible based on the eye signals alone, or on the peri-auricular muscle signals alone. For example, the weight may be inversely related to the measurement error of the periauricular muscle signals, relative to the measurement error of the eye-movement signal.

In some examples, sound processing system 100 comprises electrodes for measuring brain signals of the user. For instance, electrodes 106 may include electrodes for generating an EEG signals of the user. The electrodes for generating the EEG may be in the ear canal of the user. Furthermore, in this example, processors 102 may generate, based on the brain signals and the periauricular muscle signals, a combined signal. Processors 102 may use the combined signal to generate a more accurate and precise estimate of the angle corresponding to the direction in which the user's auditory attention is oriented, than might be achievable using either type of signal alone. For example, the mathematical combination of the EEG and periauricular-muscle signals may take the same form as described in Eq. 10, with the angle estimate computed using eye signals replaced by an angle estimate computed using EEG signals. The latter estimate may be computed using existing techniques for processing EEG signals such as, for example, as described in Wong et al. "Decoding Speech Sound Source Direction from Electroencephalography Data," ARO MidWinter Meeting, February 2016 (2016). As described in Wong, subjects kept their eyes fixated straight ahead while 64-channel EEG was recorded. A 3-level wavelet decomposition was then performed to split the data into 0-4, 4-8 Hz, 8-16 Hz and 16-32 Hz bands. For each band, the 4 independent components that had the largest power were taken. Over data segments of 5 seconds, the power within each component was then computed for each band. A deep neural network was trained on these features, using stochastic backpropagation. The output of the network was the angle of the incoming sound source.

In some examples, sound processing system 100 comprises sensors for measuring head signals. The head signals of the user are indicative of head movements and/or head positions of the user. In some examples, sound processing system 100 comprises accelerometers, gyroscopes, or other types of sensors to determine the head signals. Processors 102 may generate, based on the head signals and the periauricular muscle signals, a combined signal that provides a more accurate and precise estimate of the angle corresponding to the direction in which the user's auditory attention is oriented. For example, an estimate of said angle computed using head-motion signals alone can be combined mathematically with an estimate of the angle computed using periauricular muscle signals alone following an equation similar to Eq. 10, but with the angle estimate based on eye signals replaced by an angle estimate based on head movements. Alternatively, or in addition, head-motion signals can be used in a similar fashion.

In the example of FIG. 9, processors 102 control, based on the estimate of the angle, an operating characteristic of sound processing system 100 (904). In some examples, the operating characteristic is a relative volume of sounds at a target angle. The target angle corresponds to the estimate of the angle corresponding to the direction of the current auditory attention locus of the user with respect to the reference point or plane. In such examples, as part of controlling the operating characteristic of sound processing system 100, processors 102 selectively amplify sounds at a target angle relative to one or more non-target angles. In some examples, processors 102 selectively attenuate sounds at a non-target angle relative to the target angle.

In some examples, as part of controlling the operating characteristics, processors 102 selectively amplify sounds in a target spatial region relative to one or more non-target spatial regions. The target spatial region is defined by the direction of the current auditory attention locus of the user and a distance of the current auditory attention locus of the user relative to a reference points or plane. In some examples, processors 102 selectively attenuate sounds in a non-target spatial region relative to one or more target spatial regions.

In some examples, as part of controlling the operating characteristics of sound processing system 100, processors 102 may reproduce sounds recorded on at least a first track of recorded audio data and a second track of the recorded audio data. In this example, the first track and the second track correspond to sound sources at different positions. In this example, processors 102 selectively amplify or selectively attenuate the first track or the second track depending on the current auditory attention locus of the user.

Furthermore, in some examples, prior to performing the actions shown in FIG. 9, sound processing system 100 may perform a calibration process. Sound processing system 100 may perform the calibration process in various ways. For example, processors 102 may estimate the angle of a sound relative to the reference point or plane. Processors 102 may estimate the angle of sound in the manner described elsewhere in this disclosure. Additionally, processors 102 may compare the angle of the sound with the angle corresponding to the direction of the user's auditory attention, which has been estimated using the periauricular muscle signals, in order to compute an error signal. For example, the error signal may be computed as the arithmetic difference between the measured angle of the sound, and the estimated angle of the user's auditory attention. Furthermore, in this example, processors 102 may use the error signal to initialize or calibrate a process used to compute, based on the periauricular muscle signals, the estimate of the angle corresponding to the direction of the user's auditory attention. For example, the error signal defined above may be subtracted from subsequent user's auditory-attention angle estimates computed using periauricular muscle signals, so that the auditory-attention angle estimates are properly "corrected" or "calibrated".

In some examples of the calibration process, processors 102 estimate a distance of a sound source relative to the reference point or plane. Processors 102 may estimate the distance in the manner described elsewhere in this disclosure. Additionally, processors 102 may compare the estimated distance of the sound source with the signals from the periauricular muscles in order to compute an error signal. For example, the error signal may be computed as the arithmetic difference between the estimate of the sound-source distance computed based on other signals than the periauricular muscles, and the distance of the user's auditory attention target computed based on the periauricular muscle signals. Processors 102 may then use the error signal to initialize or calibrate a process used to compute, based on the periauricular muscle signals, the estimate of the distance. For example, the error signal defined above in this paragraph may be subtracted from subsequent distance estimates computed based on periauricular muscle signals, so that the latter estimates are properly "corrected" or "calibrated".

Figure 10A:
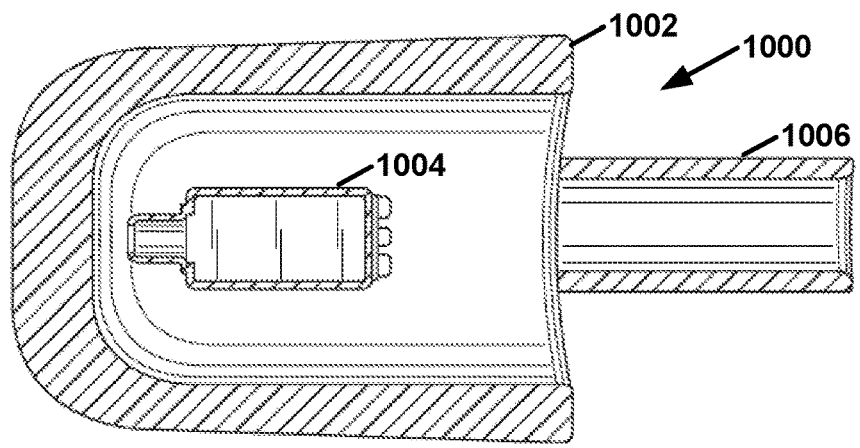
FIG. 10A is a cross section view of an example ear-wearable device, in accordance with a technique of this disclosure.
Figure 10B:
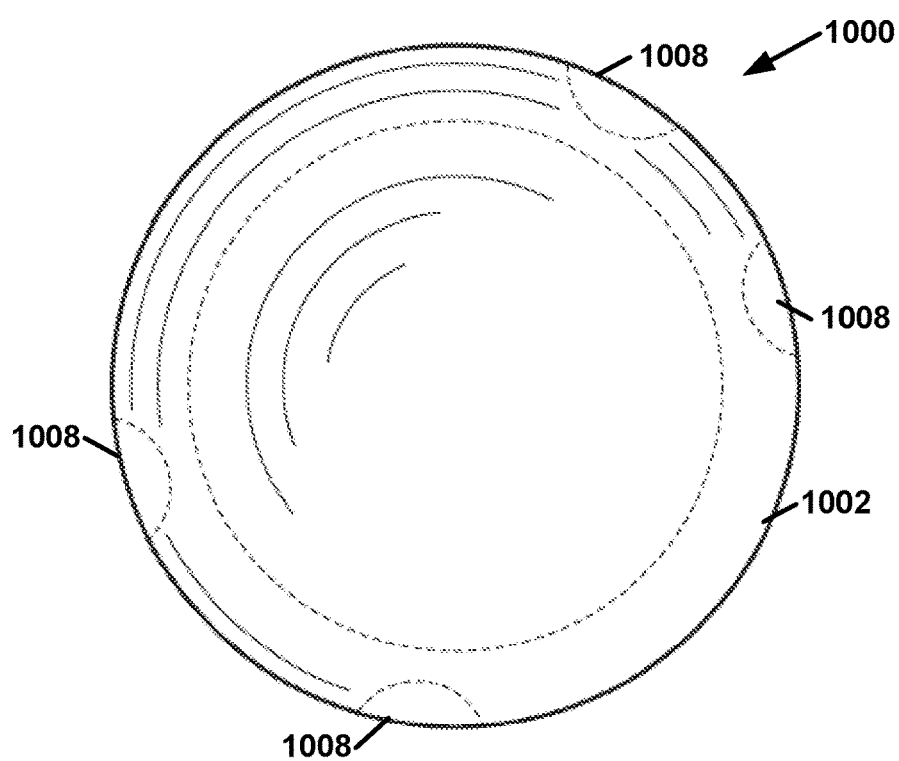
FIG. 10B is a top view of an example ear-wearable device, in accordance with a technique of this disclosure.
Figure 10C:
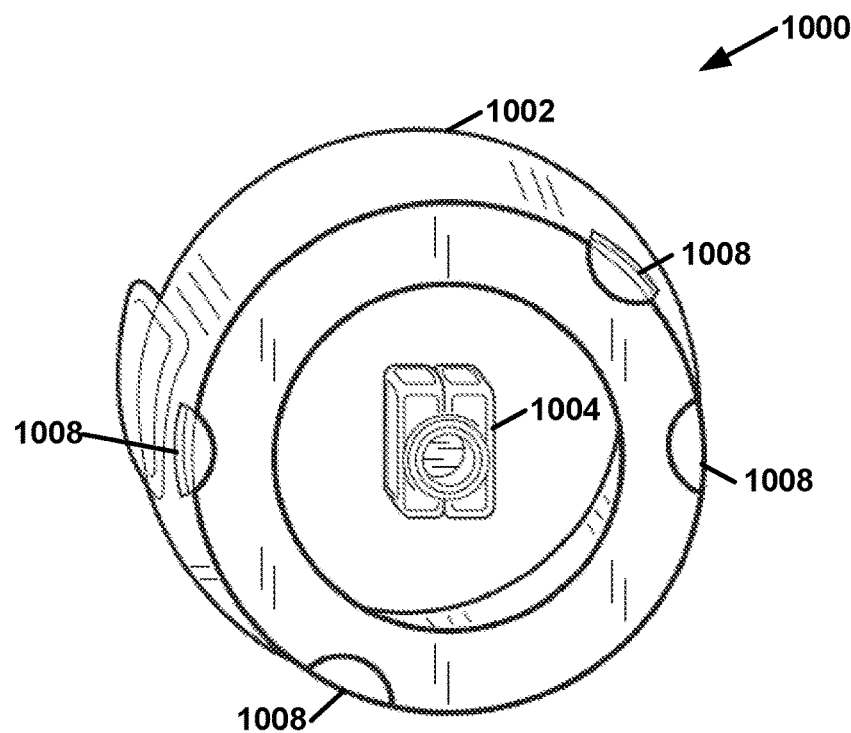
FIG. 10C is a top-cross section view of an example ear-wearable device, in accordance with a technique of this disclosure.
Figure 10D:
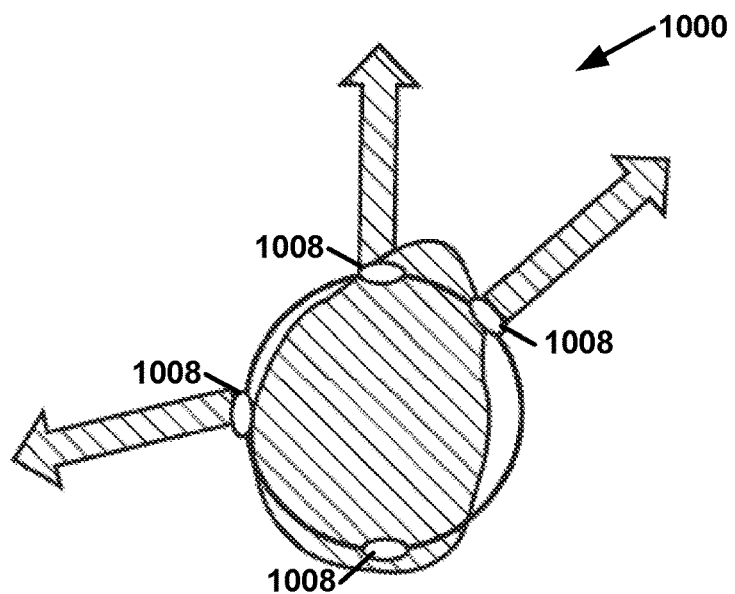
FIG. 10D is an outside section view of an example ear-wearable device, in accordance with a technique of this disclosure.

FIG. 10A is a cross section view of an example ear-wearable device 1000, in accordance with a technique of this disclosure. FIG. 10B is a top view of an example ear-wearable device 1000, in accordance with a technique of this disclosure. FIG. 10C is a top-cross section view of example ear-wearable device 1000, in accordance with a technique of this disclosure. FIG. 10D is an outside section view of example ear-wearable device 1000, in accordance with a technique of this disclosure.

In the example of FIGS. 10A-10D, ear-wearable device 1000 comprises a soft shell 1002, a receiver 1004, and a tab 1006. Receiver 1004 may be a speaker that outputs sound. Additionally, tab 1006 is placed at the lowest part of the ear, between the anti-tragus and tragus. This way, electrodes 1008 line-up with the tendon insertions of the peri-auricular muscles. In the example of FIG. 10A-10D, the walls of shell 1002 may be 2-mm thick, with a 1-mm pocket for electrodes 1008. Electrodes 1008 may comprise 2-mm in diameter gold balls that seat in shell 1002 and stick out into the ear minimally.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

In this disclosure, ordinal terms such as "first," "second," "third," and so on, are not necessarily indicators of positions within an order, but rather may simply be used to distinguish different instances of the same thing. Examples provided in this disclosure may be used together, separately, or in various combinations.

Various examples have been described. These and other examples are within the scope of the following claims.

What is claimed is:

1. A method comprising:
measuring one or more periauricular muscle signals from one or more periauricular muscles of a user;
computing, based on the periauricular muscle signals, an estimate of an angle corresponding to a direction of a current auditory attention locus of the user with respect to a reference point or plane; and
controlling, based on the estimate of the angle, an operating characteristic of a sound processing system.

2. The method of claim 1, wherein measuring the periauricular muscle signals comprises measuring a periauricular muscle signal from at least one anterior auricular muscle and at least one posterior auricular muscle on a same side of a head of the user.

3. The method of claim 1, wherein measuring the periauricular muscle signals comprises:
measuring one or more signals from one or more periauricular muscles on a right side of the head of the user; and
measuring one or more signals from one or more periauricular muscles on a left side of the head of the user.

4. The method of claim 3,
wherein measuring the one or more signals from the one or more periauricular muscles on the right side of the head of the user comprises measuring signals from an anterior auricular muscle and a posterior auricular muscle on the right side of the head of the user; and
wherein measuring the one or more signals from the one or more periauricular muscles on the left side of the head of the user comprises measuring signals from an anterior auricular muscle and a posterior auricular muscle on the left side of the head of the user.

5. The method of claim 3, further comprising:
computing, based on the one or more signals from the one or more periauricular muscles on the right side of the head of the user and the one or more signals from the one or more periauricular muscles on the left side of the head of the user, an estimate of a distance corresponding to the current auditory attention locus of the user.

6. The method of claim 1, further comprising using the one or more periauricular muscle signals to compute an estimate of an elevation angle corresponding to the current auditory attention locus of the user, relative to the reference point or plane, wherein a component of the angle is the elevation angle.

7. The method of claim 6, wherein:
measuring the set of one or more periauricular muscle signals comprises measuring a signal from a superior auricular muscle, and,
the method further comprises using the signal from the superior auricular muscle to compute the estimate of the elevation angle corresponding to the current auditory attention locus of the user, relative to the reference point or plane.

8. The method of claim 1, measuring the set of one or more periauricular muscle signals comprises measuring, with a set of one or more electrodes, the one or more periauricular muscle signals.

9. The method of claim 8, wherein at least one of:
the set of electrodes includes one or more electrodes located at least partly inside an ear canal of the user;
the set of electrodes includes one or more electrodes located at least partly inside a concha of the user;
the set of electrodes includes one or more electrodes located at least partly atop or behind a pinna of the user, or
the set of electrodes includes one or more electrodes located at least partly anterior to an ear canal and pinna of the user.

10. The method of claim 1, wherein the sound processing system comprises at least one hearing assistance device.

11. The method of claim 1, wherein the sound processing system comprises:
at least one headphone; and
at least one electrode for measuring one or more of the signals from the one or more periauricular muscles.

12. The method of claim 1, wherein controlling the operating characteristic of the sound processing system comprises at least one of:
selectively amplifying sounds at a target angle relative to one or more non-target angles, wherein the target angle corresponds to the estimate of the angle corresponding to the direction of the current auditory attention locus of the user with respect to the reference point or plane.

13. The method of claim 1, wherein controlling the operating characteristic of the sound processing system comprises selectively attenuating sounds at a non-target angle relative to a target angle, wherein the target angle corresponds to the estimate of the angle corresponding to the direction of the current auditory attention locus of the user with respect to the reference point or plane.

14. The method of claim 1, wherein controlling the operating characteristic of the sound processing system comprises selectively amplifying sounds in a target spatial region relative to one or more non-target spatial regions, wherein the target spatial region is defined by the direction of the current auditory attention locus of the user and a distance of the current auditory attention locus of the user relative to the reference point or plane.

15. The method of claim 1, wherein controlling the operating characteristic of the sound processing system comprises selectively attenuating sounds in a non-target spatial region relative to one or more target spatial regions, wherein the target spatial region is defined by the direction of the current auditory attention locus of the user and a distance of the current auditory attention locus of the user relative to the reference point or plane.

16. The method of claim 1, where the sound processing system operates on virtual sound sources.

17. The method of claim 1, wherein:
the method further comprises:
measuring eye signals, the eye signals comprising at least one of eye-movement signals of the user or eye-position signals of the user; and
generating, based on the eye signals and the periauricular muscle signals, a combined signal, and
computing the estimate of the angle comprises computing, based on the combined signal, the estimate of the angle corresponding to the direction of the current auditory attention locus of the user relative to the reference point or plane.

18. The method of claim 1, wherein the method further comprises:
measuring eye signals, the eye signals comprising at least one of eye-movement signals of the user or eye-position signals of the user;
generating, based on the eye signals and the periauricular muscle signals, a combined signal; and
computing, based on the combined signal, an estimate of a distance to the current auditory attention locus of the user relative to the reference point or plane.

19. The method of claim 1, wherein:
the method further comprises:
measuring brain signals of the user; and
generating, based on the brain signals and the periauricular muscle signals, a combined signal; and
computing the estimate of the angle comprises using the combined signal to generate the estimate of the angle.

20. The method of claim 1, wherein the method further comprises:
measuring brain signals of the user;
generating, based on the brain signals and the periauricular muscle signals, a combined signal; and
computing, based on the combined signal, an estimate of a distance to the current auditory attention locus of the user relative to the reference point or plane.

21. The method of claim 1, wherein:
the method further comprises:
measuring head signals of the user, the head signals of the user being indicative of head movements and/or head positions of the user;
generating, based on the head signals and the periauricular muscle signals, a combined signal; and
computing the estimate of the angle comprises computing, based on the combined signal, the estimate of the angle corresponding to the direction of the current auditory attention locus of the user.

22. The method of claim 1, wherein the method further comprises:
measuring head signals of the user, the head signals of the user being indicative of head movements and/or head positions of the user;
generating, based on the head signals and the periauricular muscle signals, a combined signal; and computing, based on the combined signal, an estimate of a distance to the current auditory attention locus of the user relative to the reference point or plane.

23. The method of claim 1, wherein controlling the operating characteristic of the sound processing system comprises:
reproducing sounds recorded on at least a first track and a second track, wherein the first track and the second track correspond to sound sources at different positions; and
selectively amplifying or selectively attenuating the first track or the second track based on the current auditory attention locus of the user.

24. The method of claim 1, further comprising
estimating the angle of a sound relative to the reference point or plane;
comparing the angle of the sound with the periauricular muscle signals in order to compute an error signal; and
at least one of:
using the error signal to initialize or calibrate a process used to compute, based on the periauricular muscle signals, the estimate of the angle; or
using the error signal to initialize or calibrate a process used to estimate a distance to the current auditory attention locus of the user.

25. The method of claim 1, further comprising:
estimating a distance of a sound source relative to the reference point or plane;
comparing the estimated distance of the sound source with the signals from the periauricular muscles in order to compute an error signal; and
at least one of:
using the error signal to initialize or calibrate a process used to compute, based on the periauricular muscle signals, the estimate of the angle; or
using the error signal to initialize or calibrate a process used to estimate a distance to the current auditory attention locus of the user.

26. A sound processing system comprising:
one or more electrodes configured to measure one or more periauricular muscle signals from one or more periauricular muscles of a user; and
one or more processors configured to:
compute, based on the periauricular muscle signals, an estimate of an angle corresponding to a direction of a current auditory attention locus of the user with respect to a reference point or plane; and
control, based on the estimate of the angle, an operating characteristic of a sound processing system.

27. The sound processing system of claim 26, wherein the one or more electrodes are configured to:
measure one or more signals from one or more periauricular muscles on a right side of the head of the user; and
measure one or more signals from one or more periauricular muscles on a left side of the head of the user.

28. The sound processing system of claim 27, wherein the one or more processors are configured to compute, based on the one or more signals from the one or more periauricular muscles on the right side of the head of the user and the one or more signals from the one or more periauricular muscles on the left side of the head of the user, an estimate of a distance corresponding to the current auditory attention locus of the user.

29. The sound processing system of claim 26, wherein the one or more processors are further configured to use the one or more periauricular muscle signals to compute an estimate of an elevation angle corresponding to the current auditory attention locus of the user, relative to the reference point or plane, wherein a component of the angle is the elevation angle.

30. The sound processing system of claim 26, wherein:
the one or more electrodes are configured to measure eye signals, the eye signals comprising at least one of eye-movement signals of the user or eye-position signals of the user,
the one or more processors are further configured to generate, based on the eye signals and the periauricular muscle signals, a combined signal, and
the one or more processors are configured such that, as part of computing the estimate of the angle, the one or more processors compute, based on the combined signal, the estimate of the angle corresponding to the direction of the current auditory attention locus of the user relative to the reference point or plane.

31. The sound processing system of claim 26, wherein:
the one or more electrodes are configured to measure brain signals of the user; and
the one or more processors are configured to generate, based on the brain signals and the periauricular muscle signals, a combined signal; and
the one or more processors are configured such that, as part of computing the estimate of the angle, the one or more processors are configured to use the combined signal to generate the estimate of the angle.

32. A sound processing system comprising:
means for measuring one or more periauricular muscle signals from one or more periauricular muscles of a user;
means for computing, based on the periauricular muscle signals, an estimate of an angle corresponding to a direction of a current auditory attention locus of the user with respect to a reference point or plane; and
means for controlling, based on the estimate of the angle, an operating characteristic of a sound processing system.

33. A computer-readable storage medium having stored thereon instructions that, when executed, cause a sound processing system to:
measure one or more periauricular muscle signals from one or more periauricular muscles of a user;
compute, based on the periauricular muscle signals, an estimate of an angle corresponding to a direction of a current auditory attention locus of the user with respect to a reference point or plane; and
control, based on the estimate of the angle, an operating characteristic of a sound processing system.

\* \* \* \* \*